US008268749B2

(12) United States Patent  (10) Patent No.: US 8,268,749 B2
Wright et al.  (45) Date of Patent: Sep. 18, 2012

(54) FAST SYMPTOM GLYPHOSATE FORMULATIONS

(75) Inventors: Daniel R. Wright, St. Louis, MO (US); Joseph J. Sandbrink, Chesterfield, MO (US); Paul G. Ratliff, Olivette, MO (US); Bryan A. Kliewer, Delegacion Miguel (MX); Dawn Y. Wyse-Pester, O'Fallon, MO (US)

(73) Assignee: Monsanto Technology LLC, St. Louis, MO (US)

( * ) Notice: Subject to any disclaimer, the term of this patent is extended or adjusted under 35 U.S.C. 154(b) by 276 days.

(21) Appl. No.: 11/227,577

(22) Filed: Sep. 15, 2005

(65) Prior Publication Data

US 2006/0063678 A1 Mar. 23, 2006

Related U.S. Application Data

(60) Provisional application No. 60/610,695, filed on Sep. 17, 2004.

(51) Int. Cl.
*A01N 57/00* (2006.01)
(52) U.S. Cl. ........................................ 504/127; 504/119
(58) Field of Classification Search ............... 504/116.1, 504/127, 119
See application file for complete search history.

(56) References Cited

U.S. PATENT DOCUMENTS

| | | | |
|---|---|---|---|
| 2,622,975 A | 12/1952 | Zimmerman et al. | |
| 2,626,862 A | 1/1953 | Zimmerman et al. | |
| 3,455,675 A | 7/1969 | Irani | |
| 3,556,762 A | 1/1971 | Hamm | |
| 3,645,716 A | 2/1972 | Rutkowski | |
| 3,799,758 A | 3/1974 | Franz | |
| 3,868,407 A | 2/1975 | Franz et al. | |
| 3,888,915 A | 6/1975 | Alt | |
| 3,929,450 A | 12/1975 | Hamm et al. | |
| 3,977,860 A | 8/1976 | Franz | |
| 3,988,142 A | 10/1976 | Franz | |
| 4,134,754 A | 1/1979 | Hoffmann | |
| 4,140,513 A | 2/1979 | Prill | |
| 4,147,719 A | 4/1979 | Franz | |
| 4,159,901 A | 7/1979 | Beestman et al. | |
| 4,315,765 A | 2/1982 | Large | |
| 4,341,549 A | 7/1982 | Large et al. | |
| 4,376,644 A | 3/1983 | Large | |
| 4,384,880 A | 5/1983 | Large | |
| 4,397,676 A | 8/1983 | Bakel | |
| 4,405,531 A | 9/1983 | Franz | |
| 4,436,547 A | 3/1984 | Sampson | |
| 4,437,874 A | 3/1984 | Large | |
| 4,440,562 A | 4/1984 | Prill | |
| 4,445,927 A | 5/1984 | Gimesi et al. | |
| 4,464,194 A | 8/1984 | Prisbylla | |
| 4,475,942 A | 10/1984 | Bakel | |
| 4,481,026 A | 11/1984 | Prisbylla | |
| 4,525,202 A | 6/1985 | Large et al. | |
| 4,528,023 A | 7/1985 | Ahle | |
| 4,626,274 A | 12/1986 | Hausmann et al. | |
| 4,738,708 A * | 4/1988 | Borrod et al. ................. | 504/203 |
| 4,834,908 A | 5/1989 | Hazen et al. | |
| 4,975,110 A | 12/1990 | Puritch et al. | |
| 5,035,741 A | 7/1991 | Puritch et al. | |
| 5,037,654 A | 8/1991 | Puritch et al. | |
| 5,078,782 A | 1/1992 | Nielsen et al. | |
| 5,098,467 A | 3/1992 | Puritch et al. | |
| 5,098,468 A | 3/1992 | Puritch et al. | |
| 5,106,410 A | 4/1992 | Puritch et al. | |
| 5,147,444 A | 9/1992 | Decor et al. | |
| 5,196,044 A | 3/1993 | Caulder et al. | |
| 5,242,891 A | 9/1993 | Larsen et al. | |
| 5,284,819 A * | 2/1994 | Zorner et al. ................. | 504/127 |
| 5,342,630 A | 8/1994 | Jones | |
| 5,397,766 A | 3/1995 | Dexter | |
| 5,631,290 A | 5/1997 | Almond et al. | |
| 5,663,117 A | 9/1997 | Warner | |
| 5,750,468 A | 5/1998 | Wright et al. | |
| 5,795,847 A | 8/1998 | Nielsen et al. | |
| 5,888,934 A | 3/1999 | Townson et al. | |
| 5,912,209 A | 6/1999 | Kassebaum et al. | |
| 5,919,733 A | 7/1999 | Sedun et al. | |
| 5,928,995 A * | 7/1999 | Lichtner, Jr. ................. | 504/128 |

(Continued)

FOREIGN PATENT DOCUMENTS

AU 586293 6/1989

(Continued)

OTHER PUBLICATIONS

Hartzler, B., Which Glyphosate Product is Best?, Iowa State University, Weed Science, 2001, URL <http://www.weeds.iastate.edu/mgmt/2001/glyphosateformulations.htm>.* Hager, A., Herbicide Formulations and Calculations:Active Ingredient or Acid Equivalent?, University of Illinois, 2000, URL <http://www.ipm.uiuc.edu/bulletin/pastpest/articles/200002j.html>.*
Liu, Z.Q., et al., "Influence of Surfactant Mixtures on Cuticular Uptake of Glyphosate into Grasses," 1999, Pesticide Technology, Proc. 52nd N.Z. Plant Protection Conf., pp. 228-233.
Pline, W.A., et al., "Weed and Herbicide-Resistant Soybean (Glycine max) Response to Glufosinate and Glyphosate Plus Ammonium Sulfate and Perlargonic Acid," 2000, Weed Technology, vol. 14, pp. 667-674.

(Continued)

*Primary Examiner* — Fereydoun G Sajjadi
*Assistant Examiner* — Danielle Sullivan
(74) *Attorney, Agent, or Firm* — Senniger Powers LLP; Joseph A. Schaper

(57) ABSTRACT

Aqueous herbicidal glyphosate compositions are provided, particularly sprayable, ready-to-use (RTU) formulations that are capable of inducing early visually apparent phytotoxic effects while minimizing antagonism to the glyphosate component of the composition and preserving the equally desirable attribute of prolonged control of the treated plants. The compositions combine a glyphosate component and a fatty acid component as a fast symptomology active ingredient and, in one embodiment, are enhanced by the concentration of the fatty acid component utilized and the inclusion of an agronomically acceptable inorganic ammonium salt, preferably ammonium sulfate. In another embodiment, the compositions of the present invention include a nonionic surfactant component comprising certain water-soluble, alkoxylated alcohols.

46 Claims, No Drawings

U.S. PATENT DOCUMENTS

| | | | |
|---|---|---|---|
| 5,945,377 A | 8/1999 | Penner et al. | |
| 5,948,731 A | 9/1999 | Evans et al. | |
| 5,994,269 A | 11/1999 | Bugg et al. | |
| 5,998,332 A | 12/1999 | Sato et al. | |
| 6,010,979 A | 1/2000 | Osborn et al. | |
| 6,117,823 A | 9/2000 | Smiley | |
| 6,127,318 A | 10/2000 | Sato et al. | |
| 6,165,939 A | 12/2000 | Agbaje et al. | |
| 6,180,566 B1 | 1/2001 | Nielsen et al. | |
| 6,218,336 B1 | 4/2001 | Coleman | |
| 6,323,153 B1 | 11/2001 | Smiley | |
| 6,323,156 B1 | 11/2001 | Smiley | |
| 6,468,944 B1 | 10/2002 | Bugg et al. | |
| 6,503,869 B1 | 1/2003 | Beste et al. | |
| 6,509,297 B1 | 1/2003 | Coleman | |
| 6,608,003 B2 | 8/2003 | Smiley | |
| 6,624,128 B1 | 9/2003 | Smiley | |
| 6,710,018 B2 | 3/2004 | Smiley | |
| 6,770,594 B2 | 8/2004 | Bickers et al. | |
| 6,930,075 B1 | 8/2005 | Mason | |
| 6,992,045 B2 | 1/2006 | Xu et al. | |
| 7,008,904 B2 | 3/2006 | Crockett et al. | |
| 2002/0123430 A1* | 9/2002 | Xu et al. | 504/206 |
| 2003/0153461 A1* | 8/2003 | Parrish et al. | 504/116.1 |

FOREIGN PATENT DOCUMENTS

| | | |
|---|---|---|
| EP | 0 577 914 A1 | 1/1994 |
| EP | 0 688 165 B1 | 6/1998 |
| FR | 2 589 328 A1 | 5/1987 |
| GB | 2 169 806 A | 7/1986 |
| GB | 2 247 621 A | 3/1992 |
| JP | 59-193804 A | 11/1984 |
| JP | 59-193809 A | 11/1984 |
| JP | 59-199608 A | 11/1984 |
| JP | 59-199609 A | 11/1984 |
| JP | 61-106501 A | 5/1986 |
| JP | 61-289004 A | 12/1986 |
| JP | 63-080846 A | 4/1988 |
| JP | 8-217605 A | 8/1996 |
| JP | 2003-342104 A | 12/2003 |
| WO | WO 89/03178 A1 | 4/1989 |
| WO | WO 90/07275 A1 | 7/1990 |
| WO | WO 92/06596 A1 | 4/1992 |
| WO | WO 92/07467 A1 | 5/1992 |
| WO | WO 92/11764 A1 | 7/1992 |
| WO | WO 94/18831 A1 | 9/1994 |
| WO | WO 97/41730 A1 | 11/1997 |
| WO | WO 2004/019684 A2 | 3/2004 |

OTHER PUBLICATIONS

International Search Report for PCT/US2005/033026 dated Feb. 21, 2006, 4 pgs.

Arnold, K.A., et al., "Improved Early Symptom Development with a Ready-To-Use Glyphosate Formulation by Addition of Fatty Acid," *Pesticide Science*, 38(2-3), pp. 270-271 (1993).

Schilling et al., "Influence of Surfactants and Additives on Phytotoxicity of Glyphosate to Torpedograss[1]," J. Aqua. Plant Mgt., 1990, vol. 28, pp. 23-27.

Turner "Effects on Glyphosate Performance of Formulation, Additives and Mixing with other Herbicides," The Herbicide Glyophosate, Butterworth & Co., Ltd., 1985, pp. 221-240.

Wells, A.J., "Adjuvants, Glyphosate Efficacy and Post-Spraying Rainfall," Plant Protection Quarterly, 1989, vol. 4(4), pp. 158-164.

The Agrochemicals Handbook, 2nd Edition, Hartley and Kidd, editors; The Royal Society of Chemistry, Nottingham, England, 1987, pp. A045, A138.

"Effect of Salt Additives on Activity and Movement of Glyphosate and MSMA in Purple Nutsedge" Technical Bulletin 140 of the Mississippi Agricultural and Forestry Experiment Station, Apr. 1987, Mississippi State University, Mississippi State, MS 39762.

KGRO Grass & Weed Killer (sold in USA).

Statesman Weed & Grass Killer Ready-to-Use (sold in USA).

Roundup Ready-to-Use Weedkiller (sold in EU member countries).

Roundup Ready-to-Use (sold in Canada).

Roundup Ready-to-use Weed & Grass Killer/KGRO Fence & Walk Edger (sold in USA).

* cited by examiner

FAST SYMPTOM GLYPHOSATE FORMULATIONS

REFERENCE TO RELATED APPLICATIONS

This application claims the benefit of U.S. Provisional Application Ser. No. 60/610,695, filed Sep. 17, 2004, the entire contents of which are incorporated herein by reference.

BACKGROUND OF THE INVENTION

The present invention relates generally to fast-acting herbicidal compositions or formulations containing glyphosate, and to methods of using such compositions to kill or control the growth and proliferation of unwanted plants.

Herbicidal compositions containing the herbicide N-(phosphonomethyl)glycine (commonly referred to as glyphosate) or its derivatives are useful for killing or suppressing the growth of unwanted plants such as grasses, weeds and the like. The herbicidal properties of glyphosate and its derivatives were discovered by Franz and patented in U.S. Pat. Nos. 3,799,758 and 4,405,531. Glyphosate herbicidal formulations are typically applied to the foliar tissues (i.e., the leaves or other photosynthesizing organs) of the target plant by spray application. After application, the glyphosate is absorbed by the foliar tissues and translocated throughout the plant. Glyphosate noncompetitively blocks an important biochemical pathway which is common to virtually all plants, but which is absent in animals. Although glyphosate is very effective in killing or controlling the growth of unwanted plants, the uptake (i.e., absorption) of glyphosate by the plant foliar tissue and translocation of glyphosate throughout the plant is relatively slow. Visually apparent phytotoxic effects or burndown symptoms (e.g., yellowing, browning, wilting etc.) may not appear until one week or more after a plant has been treated with glyphosate or its derivatives.

Given the relatively limited water solubility of the organic acid N-(phosphonomethyl)glycine, aqueous herbicidal compositions are typically formulated using one or more of the more water-soluble and acceptable salts or other derivatives of glyphosate. Furthermore, these compositions typically further contain one or more surfactants to enhance their effectiveness for foliar application. When water is added to a composition formulated with surfactants, the resulting sprayable composition more easily and effectively covers the foliar tissues of plants. Therefore, glyphosate salts, have been formulated with various surfactants such as polyoxyalkylene-type surfactants (e.g., with a polyoxyalkylene alkylamine, and in particular a polyoxyethylene tallowamine). Monsanto Company markets commercial formulations of glyphosate with such surfactants under the trademark ROUNDUP.

Nevertheless, because of the somewhat slow development of visual symptoms of plant suppression or death that result when glyphosate is utilized alone or even with a surfactant, various alternative herbicidal formulations have been suggested to induce earlier visual symptoms of treatment. Early symptom-producing or fast-acting, ready-to-use (RTU) compositions are particularly desired in the lawn and garden market where the consumer appreciates relatively immediate evidence that the product is having the desired effect.

Attempts at inducing earlier visual symptomology have included combining glyphosate or its derivatives with certain fatty acids or their herbicidally active salts, for example, pelargonic acid (PA; also referred to as nonanoic acid), capric acid (also referred to as decanoic acid) and mixtures of such fatty acids or salts thereof as described, for example, in U.S. Pat. Nos. 5,196,044 (Caulder, et al.) and 5,994,269 (Bugg, et al.), International Publication No. WO 92/07467, European Patent Application Publication No. 0 577 914, and by Kristin A. Arnold, et al. in "Improved Early Symptom Development with a Ready-To-Use Glyphosate Formulation by Addition of Fatty Acid," *Pesticide Science,* 38(2-3), pp. 270-272 (1993). It is suggested that such a combination provides a herbicidal formulation capable of inducing fast symptomology in the treated plants due to the fatty acid component and prolonged control due to the glyphosate component. Indeed some success has been achieved along these lines in RTU formulations available from Monsanto Company and other manufacturers.

However, despite some degree of success in providing herbicidal compositions that accelerate the appearance of visual phytotoxic effects, there remains a need, particularly in the RTU market segment, for improved glyphosate formulations providing even faster symptomology. Moreover, previous attempts, while inducing earlier visual effects on treated plants, have sometimes suffered from less than expected or desired long-term control, perhaps due to unintended antagonism to the glyphosate component by other ingredients of the herbicidal composition. Still further, difficulty has been encountered in providing fast-acting glyphosate compositions that resist separation of the active ingredients and other components of the formulation from the aqueous solution upon prolonged storage and that can be readily formulated as a concentrate.

SUMMARY OF THE INVENTION

Among the objects of the present invention, therefore, are the provision of aqueous herbicidal glyphosate compositions capable of inducing early appearance of visual phytotoxic effects in treated plants; the provision of such compositions exhibiting overall superior herbicidal activity and long-term control of unwanted plants; the provision of such compositions in which antagonism to long-term control of unwanted plants by the glyphosate component of the composition is reduced or eliminated; the provision of such aqueous herbicidal glyphosate compositions that may be readily formulated as a concentrate or as a sprayable ready-to-use (RTU) product; the provision of such compositions that are resistant to separation of the components of the formulation from the aqueous solution upon prolonged storage; and the provision of methods for killing or controlling the growth of a broad spectrum of unwanted plants species by applying to the foliar tissues of the plants aqueous herbicidal glyphosate compositions of the present invention.

Briefly, therefore, the present invention is directed to an aqueous ready-to-use herbicidal composition useful for killing or controlling the growth of unwanted plants. The RTU composition comprises from about 0.1% to about 5% by weight acid equivalent (a.e.) of a glyphosate component comprising N-(phosphonomethyl)glycine, an agronomically acceptable salt of N-(phosphonomethyl)glycine or a mixture thereof; at least about 1.5% and up to about 5% by weight (a.e.) of a fatty acid component predominantly comprising at least one $C_8$ to $C_{12}$ saturated, straight or branched chain fatty acid or an agronomically acceptable salt thereof; and from about 0.5% to about 4% by weight of an agronomically acceptable inorganic ammonium salt.

In accordance with another embodiment of the invention, the aqueous RTU herbicidal composition comprises from about 0.1% to about 5% by weight (a.e.) of a glyphosate component comprising N-(phosphonomethyl)glycine, an agronomically acceptable salt of N-(phosphonomethyl)glycine or a mixture thereof; from about 0.25% to about 5% by weight (a.e.) of a fatty acid component predominantly comprising at least one $C_8$ to $C_{12}$ saturated, straight or branched chain fatty acid or an agronomically acceptable salt thereof; and from about 1% to about 4% by weight of ammonium sulfate.

In accordance with one preferred embodiment, the aqueous RTU herbicidal composition comprises from about 1% to about 5% by weight (a.e.) of a glyphosate component predominantly comprising a salt of N-(phosphonomethyl)glycine selected from the isopropylammonium salt of N-(phosphonomethyl)glycine, the ammonium salt of N-(phosphonomethyl)glycine and the potassium salt of N-(phosphonomethyl)glycine; at least about 1.5% and up to about 3% by weight (a.e.) of a fatty acid component predominantly comprising pelargonic acid or an agronomically acceptable salt thereof; and from about 1.5% to about 3% by weight of ammonium sulfate.

The present invention is further directed to an aqueous herbicidal composition useful for killing or controlling the growth of unwanted plants comprising a glyphosate component comprising N-(phosphonomethyl)glycine, an agronomically acceptable salt of N-(phosphonomethyl)glycine or a mixture thereof; a fatty acid component comprising at least one saturated or unsaturated, straight or branched chain $C_5$ to $C_{18}$ fatty acid or agronomically acceptable salt thereof; and a nonionic surfactant (NIS) component comprising an alkoxylated, $C_8$ to $C_{20}$, nonaromatic alcohol with an average degree of alkoxylation such that the alcohol has a solubility in water of at least about 0.5% by weight at 25° C.

In accordance with another embodiment of the present invention, the aqueous herbicidal composition including a nonionic surfactant component comprising an alkoxylated, $C_8$ to $C_{20}$, nonaromatic alcohol is prepared in the form of an RTU composition. In one such preferred embodiment, the aqueous RTU herbicidal composition comprises from about 0.1% to about 5% by weight (a.e.) of a glyphosate component predominantly comprising a salt of N-(phosphonomethyl)glycine selected from the isopropylammonium salt of N-(phosphonomethyl)glycine, the ammonium salt of N-(phosphonomethyl)glycine and the potassium salt of N-(phosphonomethyl)glycine; from about 0.25% to 5% by weight (a.e.) of a fatty acid component predominantly comprising pelargonic acid or a salt thereof; from about 0.5% to about 12% by weight of the nonionic surfactant component predominantly comprising ethoxylated, primary or secondary, undecyl alcohol with an average degree of ethoxylation of from about 5 to about 9; and from about 0.5% to about 4% by weight of ammonium sulfate.

The present invention is further directed to methods for killing or controlling the growth of unwanted plants, comprising treating the plant by applying to the foliar of the plant an aqueous herbicidal composition in accordance with the present invention.

Other objects and features of this invention will be in part apparent and in part pointed out hereinafter.

DETAILED DESCRIPTION OF THE PREFERRED EMBODIMENTS

In accordance with the present invention, aqueous herbicidal glyphosate compositions are provided, particularly sprayable, ready-to-use (RTU) formulations that are capable of inducing early, visually apparent, phytotoxic effects while minimizing antagonism to the glyphosate component of the composition and preserving the equally desirable attribute of prolonged control of the treated plants. These formulations are based in part on the previously identified combination of a fatty acid component as a fast symptomology active ingredient with a glyphosate component capable of providing long-term control of the treated plants. However, in accordance with a first aspect of the present invention, consistent fast symptomology and overall herbicidal effectiveness are enhanced by the concentration of the fatty acid component utilized and the inclusion of an agronomically acceptable inorganic ammonium salt, preferably ammonium sulfate. By employing appreciable quantities of the fatty acid component and ammonium sulfate or other inorganic ammonium salt, a formulation is provided that further accelerates or otherwise enhances visually apparent phytotoxic effects in the treated plants. Although use of a surfactant in the compositions of the present invention is not required, use of a surfactant is preferred and, in accordance with a further aspect of the invention, it has been discovered that faster symptomology in the treated plants can be achieved by the inclusion of a nonionic surfactant component comprising certain water-soluble, alkoxylated alcohols. The present invention contemplates and provides sprayable aqueous glyphosate RTU compositions in which the components resist separation from the aqueous solution even upon prolonged storage and are suitable for formulation as a concentrate.

The herbicidal compositions of the present invention are applied as aqueous solutions or dispersions. However, the term "aqueous," as used herein, is not intended to exclude the presence of nonaqueous (i.e., organic) solvents, as long as water is present. Water is the predominant component of the aqueous RTU compositions disclosed herein.

The glyphosate component of the aqueous composition is typically primarily responsible for plant suppression or death and is instrumental in imparting long-term herbicidal control. The glyphosate component comprises N-(phosphonomethyl) glycine, a salt or other agronomically acceptable derivative of N-(phosphonomethyl)glycine which is converted to glyphosate in plant tissues or which otherwise provides glyphosate anion or a mixture thereof. In this regard it is to be noted that the term "glyphosate" or "glyphosate component" when used herein is understood to encompass N-(phosphonomethyl) glycine, such derivatives as well as mixtures thereof unless the context requires otherwise. Furthermore, the term "agronomically acceptable" includes glyphosate derivatives that allow agriculturally and economically useful herbicidal activity of an N-(phosphonomethyl)glycine anion in residential or industrial applications.

In the aqueous herbicidal compositions of the present invention, it is preferred that the glyphosate component predominantly comprise one or more of the more water-soluble salts of N-(phosphonomethyl)glycine. As used throughout this specification, the expression "predominantly comprises" means more than 50%, preferably at least about 75%, and more preferably at least about 90% by weight of the component of the herbicidal composition is made up of the specified compound(s). A glyphosate component predominantly comprising one or more of the various salts of N-(phosphonomethyl)glycine is preferred in part because their increased water solubility that allows formulation of highly concentrated herbicidal compositions that can be easily transported and readily diluted with water in the preparation of sprayable RTU compositions at the site of intended use.

Suitable salts of N-(phosphonomethyl)glycine include mono-, di- or tribasic and include organic ammonium, alkali metal, alkaline earth metal, ammonium (e.g., mono-, di- or triammonium) and sulfonium (e.g., mono-, di- or trimethylsulfonium) salts of N-(phosphonomethyl)glycine. The organic ammonium salts can comprise aliphatic or aromatic ammonium salts and can include primary, secondary, tertiary or quaternary ammonium salts. Specific representative examples of such organic ammonium salts include isopropylammonium, n-propylammonium, ethylammonium, dimethylammonium, 2-hydroxyethylammonium (also referred to as monoethanolammonium), ethylenediamine and hexamethylenediamine salts of N-(phosphonomethyl)glycine. Specific representative examples of alkali metal salts include potassium and sodium salts of N-(phosphonomethyl)glycine. In accordance with a more preferred embodiment of the invention, the glyphosate component predominantly comprises a salt of N-(phosphonomethyl)glycine selected from the potassium, monoammonium, diammonium, sodium, monoethanolammonium, n-propylammonium, isopropylammonium, ethylammonium, dimethylammonium, ethylenediamine, hexamethylenediamine and trimethylsulfonium salts and combinations thereof. Of these, the isopropylammonium, ammonium and potassium salts and combinations thereof are especially preferred.

The concentration of the glyphosate component in aqueous RTU compositions of the present invention is typically at least about 0.1% and generally from about 0.1% to about 5% by weight acid equivalent (a.e.). However, it has been observed that reduced antagonism to long-term herbicidal control (i.e., reduction in glyphosate performance) is achieved when the concentration of the glyphosate component in the RTU formulation is at least about 1% by weight (a.e.). Accordingly, the concentration of the glyphosate component in the RTU composition is preferably from about 1% to about 5% by weight (a.e.). In order to provide more economical RTU formulations providing prolonged herbicidal activity, the concentration of the glyphosate component in the RTU composition is more preferably from about 1% to about 2% by weight (a.e.), even more preferably from about 1.25% to about 2% by weight (a.e.) and optimally about 1.5% by weight (a.e.).

While ROUNDUP herbicide is a suitable source of water-soluble glyphosate salt, other formulations providing a water-soluble glyphosate salt or N-(phosphonomethyl)glycine may be employed as a starting material. Alternatively, a water-soluble glyphosate salt or an aqueous solution thereof may be prepared prior to or during the formulation of the aqueous herbicidal composition by neutralizing N-(phosphonomethyl)glycine with an appropriate base to form the corresponding salt. For example, N-(phosphonomethyl)glycine may be used as a starting material and partially or fully neutralized along with the fatty acid or fatty acid mixture of the fatty acid component during formulation of an aqueous RTU herbicidal composition.

The fatty acid component of the aqueous herbicidal composition assists in imparting rapid symptomology and more consistent herbicidal control to the composition. The fatty acid component comprises at least one saturated or unsaturated, straight or branched chain $C_5$ to $C_{18}$ fatty acid, salt, ester or other agronomically acceptable derivative thereof and can be, for example, in the epoxide, cyclopropane, methylated or hydroxylated forms. The fatty acid component may comprise various alpha monocarboxylic fatty acids such as caprylic acid ($C_8$), pelargonic acid ($C_9$), capric acid ($C_{10}$), undecanoic acid ($C_{11}$), lauric acid ($C_{12}$), palmitic acid ($C_{16}$) stearic acid, oleic acid, linoleic acid and linolenic (all $C_{18}$), their salts and mixtures thereof. Furthermore, the fatty acid component may be derived from naturally occurring oils containing fatty acid mixtures such as soybean fatty acids and coconut fatty acids and salts of such mixtures.

Suitable fatty acids, fatty acid derivatives and mixtures thereof are disclosed, for example, in U.S. Pat. No. 5,098,468 (Puritch, et al.), U.S. Pat. No. 5,106,410 (Puritch, et al.), U.S. Pat. No. 5,196,044 (Caulder, et al.), U.S. Pat. No. 5,994,269 (Bugg, et al.) and U.S. Pat. No. 6,930,075 (Mason), European Patent Application Publication No. 0 577 914, and International Publication No. WO 89/03178, the entire disclosures of which are incorporated herein by reference.

Preferably, the fatty acid component of the herbicidal composition predominantly comprises at least one $C_8$ to $C_{12}$ saturated, straight or branched chain fatty acid (e.g., caprylic acid, pelargonic acid, capric acid, undecanoic acid or lauric acid) or agronomically acceptable salt thereof. Various partial or complete salts of fatty acids or fatty acid mixtures may be used in the fatty component. Essentially any agronomically acceptable salt of the fatty acid or fatty acid mixture may be utilized in the practice of the present invention. Fatty acids and fatty acid mixtures may be neutralized with bases of various types to form the corresponding salt either prior to or during formulation of the aqueous herbicidal composition. For example, as described below, the fatty acid component may be partially or fully neutralized with a pH adjuster (e.g., potassium hydroxide) used to adjust the pH of an RTU composition during formulation. Suitable fatty acid salts include ammonium salts, alkali metal salts (e.g., potassium and sodium salts), alkaline earth metal salts of the fatty acid or fatty acid mixture as well as mixtures of such salts. Preferably, the fatty acid salts used in the practice of the present invention include the potassium and sodium salts of the fatty acid or fatty acid mixture.

In an especially preferred embodiment, the fatty acid component of the herbicidal composition predominantly comprises pelargonic acid or an agronomically acceptable salt thereof. More preferably still, the fatty acid component comprises at least about 90% by weight pelargonic acid or an agronomically acceptable salt thereof. Among the most preferred fatty acid salts are sodium and potassium pelargonate. Commercially available sources of pelargonic acid typically comprise a mixture of pelargonic acid with other fatty acids such as caprylic acid and capric acid, however, pelargonic acid nevertheless typically predominates. Commercially available sources of pelargonic acid include the products sold as AGNIQUE FAC 9 and EMERY 1202 by Cognis Corporation (Cincinnati, Ohio) and n-pelargonic acid available from Celanese Limited (Dallas, Tex.).

In accordance with one embodiment of the present invention, an agronomically acceptable inorganic ammonium salt is optionally combined with the glyphosate component and fatty acid component of the aqueous herbicidal composition. The ammonium salt, in conjunction with the fatty acid component, further accelerates the appearance of visual phytotoxic effects in the treated plants and enhances overall herbicidal efficacy. Suitable inorganic ammonium salts include ammonium sulfate, ammonium nitrate, ammonium thiocyanate, ammonium phosphate, ammonium chloride and mixtures thereof. Ammonium sulfate is particularly effective in inducing early symptomology in treated plants and for that reason is especially preferred for inclusion in the compositions of the present invention.

The aqueous herbicidal RTU compositions of the present invention typically contain at least about 0.25% by weight acid equivalent (a.e.) of the fatty acid component and, when utilized, at least about 0.5% by weight of the inorganic ammonium salt(s). Generally, RTU formulations contain from about 0.25% to about 5% by weight (a.e.) of the fatty acid component and from about 0.5% to about 4% by weight of the inorganic ammonium salt. However, early onset of phytotoxic effects in treated plants is enhanced, particularly in RTU formulations containing ammonium sulfate, when the concentration of the inorganic ammonium salt(s) and the fatty acid component (a.e.) are independently at least about 1%, preferably at least about 1.5% and especially at least about 2% by weight. Accordingly, the aqueous RTU formulation preferably comprises from about 1% to about 4%, more preferably from about 1.5% to about 3% and optimally about 2% by weight of ammonium sulfate or other inorganic ammonium salt(s) along with significant quantities of the fatty acid component, preferably at least about 1% and up to about 5%, more preferably at least about 1.5% and up to about 5%, even more preferably at least about 1.5% and up to about 3% and optimally about 2% by weight (a.e.) of the fatty acid component.

In addition to water, the glyphosate component, fatty acid component and optional inorganic ammonium salt, aqueous herbicidal compositions in accordance with the present invention may further comprise one or more optional adjuvants (e.g., surfactant), excipients, additional active herbicidal ingredients or other additives. Greater or lesser amounts of these optional ingredients may be employed as desired.

Although not required in the practice of the present invention, the aqueous herbicidal RTU compositions of the present invention preferably optionally include a surfactant component comprising one or more surfactants. Various cationic and nonionic surfactants known to enhance the effectiveness of post-emergent herbicides such as glyphosate by facilitating foliar contact with the herbicide and subsequent translocation, as well as mixtures of such surfactants, may be used in formulating the aqueous herbicidal compositions. A general requirement of suitable surfactants is adequate water and fat solubility to permit dissolution of the herbicide active ingredients and interaction of the dissolved herbicides with waxy foliar tissues when applied to plants. Generally, the surfactant component should be water-soluble and comprise one or more surfactants characterized by a solubility of at least about 0.5% by weight in water at 25° C.

Examples of the types of suitable surfactants and surfactant mixtures that may be used in the practice of the present invention include alkylamine ethoxylates and combinations of an alkylamine ethoxylate and alkylethoxylate phosphate or sulfonate ester, alkylamine oxides, alkyl glucosides, alkoxylated (e.g., ethoxylated or propoxylated) quaternary amines, dialkylacetylenes, etheramine alkoxylates, quaternary etheramine alkoxylates, trimethyl alkylammonium chlorides, trimethyl etherammonium chlorides and water-soluble, nonionic surfactants such as alcohol alkoxylates and alkylphenol alkoxylates (e.g., alkoxylated nonylphenol).

Specific examples of these types of surfactants and surfactant combinations include a blend of tallowamine ethoxylate having an average degree of ethoxylation of about 10 with an alkylethoxylate phosphate ester in polyethylene glycol (500 average molecular weight), dipropylene glycol and water solvents; and tallowamine ethoxylate having an average degree of ethoxylation of about 10.5 in dipropylene glycol solvent.

In accordance with one embodiment of the present invention, a nonionic surfactant component comprising one or more selected water-soluble, nonionic surfactants is combined with the glyphosate component and fatty acid component of the aqueous herbicidal RTU composition. More particularly, it has been discovered that a nonionic surfactant component comprising certain alkoxylated alcohols enhance the ability of the fatty acid component and the inorganic ammonium salt (e.g., ammonium sulfate), if present, to induce early visual phytotoxic effects in treated plants.

In such an embodiment, the nonionic surfactant component comprises an alkoxylated, $C_8$ to $C_{20}$, nonaromatic alcohol with a sufficient average degree of alkoxylation such that the alkoxylated alcohol has a solubility in water of at least about 0.5% by weight at 25° C. Each of the alkoxy groups independently comprises $C_2$ to $C_4$ alkylene, preferably ethylene or propylene, and the average degree of alkoxylation (e.g., ethoxylation) is typically from about 2 to about 20, preferably from about 3 to about 12, and more preferably from about 5 to about 9.

The preferred nonionic surfactants include alkoxylated alcohols having the formula:

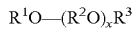

$$R^1O-(R^2O)_xR^3$$

wherein $R^1$ is nonaromatic, hydrocarbyl or substituted hydrocarbyl having from 8 to 20 carbon atoms, $R^2$ in each of the x ($R^2O$) groups is independently $C_2$ to $C_4$ alkylene, $R^3$ is hydrogen, or a linear or branched alkyl group having from 1 to about 4 carbon atoms, and the average degree of alkoxylation, x, is from about 2 to about 20. It has been observed that alkoxylated aromatic alcohols (e.g., alkoxylated nonylphenol) and highly branched, alkoxylated alcohols (e.g., alkoxylated isotridecyl alcohol) are not particularly useful in enhancing early visual phytotoxic effects in treated plants. Accordingly, in this context, it is preferred that the nonionic surfactant comprise an alkoxylated, primary or secondary, linear or minimally branched (i.e., acyclic) $C_8$ to $C_{20}$, preferably $C_{10}$ to $C_{14}$, alcohol such that the preferred $R^1$ hydrocarbyl groups are linear or minimally branched alkyl, alkenyl or alkynyl groups having from 8 to 20 carbon atoms, preferably from 10 to 14 carbon atoms, and no more than two methyl substituents. Preferably, $R^1$ is a linear or minimally branched alkyl or alkenyl group having from 8 to 20 carbon atoms, preferably from 10 to 14 carbon atoms, and no more than two methyl substituents, $R^2$ in each of the x ($R^2O$) groups is independently ethylene or propylene, preferably ethylene, $R^3$ is hydrogen, methyl or ethyl, and the average degree of alkoxylation (e.g., ethoxylation), x, is from about 3 to about 12, more preferably from about 5 to about 9. More preferably, $R^1$ is a linear or minimally branched alkyl group having from 8 to 20 carbon atoms, preferably from 10 to 14 carbon atoms, and no more than two methyl substituents, $R^2$ in each of the x ($R^2O$) groups is ethylene, $R^3$ is hydrogen or methyl, and the average degree of ethoxylation, x, is from about 3 to about 12, more preferably from about 5 to about 9.

Examples of suitable commercially available alkoxylated, linear alcohols for use in the nonionic surfactant component include alcohol ethoxylates sold under the name TOMADOL by Tomah, Products Inc. (Milton, Wis.) and including TOMADOL 25-3, TOMADOL 25-7 and TOMADOL 25-9 (made from linear $C_{12}$ to $C_{15}$ alcohols with an average of 2.8 moles, 7 moles and 9 moles of ethoxylation, respectively). Other commercially available alkoxylated, linear alcohols that may be used in the nonionic surfactant component are those in the TERGITOL series from Dow and commercially available from Sigma-Aldrich Co. (Saint Louis, Mo.), including TERGITOL-15-S-9, TERGITOL-15-S-12 and TERGITOL-15-S-15 (made from secondary, linear $C_{11}$ to $C_{15}$ alcohols with an average of 9 moles, 12.3 moles and 15.5 moles of ethoxylation, respectively); and the SURFONIC LF-X series from Huntsman Chemical Co. (Salt Lake City, Utah), including L12-7 (made from linear $C_{10}$ to $C_{12}$ alcohols with an average of 7 moles of ethoxylation), L24-7, L24-9 and L24-12 (made from linear $C_{12}$ to $C_{14}$ alcohols with an average of 7 moles, 9 moles and 12 moles of ethoxylation, respectively), and L26-6.5 (made from linear $C_{12}$ to $C_{16}$ alcohols with an average of 6.5 moles of ethoxylation).

In accordance with one preferred embodiment of the present invention, the nonionic surfactant component predominantly comprises ethoxylated, primary or secondary, undecyl alcohol with an average degree of ethoxylation of from about 3 to about 12, more preferably from about 5 to about 9. More preferably, the ethoxylated undecyl alcohol that predominates the nonionic surfactant component is an ethoxylated, primary, linear undecyl alcohol. Examples of such preferred ethoxylated, linear undecyl alcohols include TOMADOL 1-3 (average of 3 moles of ethoxylation), TOMADOL 1-5 (average of 5 moles of ethoxylation) and TOMADOL 1-9 (average of 9 moles of ethoxylation). In accordance with an especially preferred embodiment, the nonionic surfactant component of the aqueous herbicidal composition comprises at least about 90% by weight ethoxylated, primary, linear undecyl alcohol having an average degree of ethoxylation of about 7. An example of such an especially preferred ethoxylated, primary, linear undecyl alcohol is TOMADOL 1-7 (average 7 moles of ethoxylation). BEROL 537 and ETHYLAN 1008 from Akzo Nobel (Chicago, Ill.) are similar to TOMADOL 1-7, both being made from linear $C_{11}$ alcohols with an average of about 7 moles of ethoxylation.

The nonionic alkoxylated alcohol surfactant component as described above may be combined with other suitable surfactants and surfactant combinations such as those disclosed herein. However, it has been observed that combining such a nonionic surfactant with a cationic surfactant (e.g., a tallowamine ethoxylate) tends to compromise the fast development of symptoms in treated plants. Accordingly, in one preferred embodiment, the surfactant component of the aqueous RTU herbicidal composition consists essentially of an alkoxylated, nonaromatic alcohol nonionic surfactant or a mixture of such nonionic surfactants. In any event, it should be understood that surfactants are optional in the compositions of the present invention and can be omitted entirely and replaced by water.

When utilized, an effective concentration of the surfactant component in the aqueous RTU compositions can be readily determined by those skilled in the art and may vary within wide limits depending upon the type(s) of surfactants employed, the other ingredients present in the composition and the targeted herbicidal efficacy with respect to the plants to be treated. Generally, the RTU composition may contain at least about 0.5% by weight of a surfactant component. For example, in the case of a surfactant component comprising an alkylamine ethoxylate or combinations of an alkylamine ethoxylate and alkylethoxylate phosphate ester in a glycol solvent, a concentration of up to about 1% by weight may be suitably employed. However, in the case of the nonionic surfactant component comprising an alkoxylated, nonaromatic alcohol, generally slightly higher concentrations are preferred. Preferably, the concentration of the nonionic surfactant component in the RTU composition is from about 0.5% to about 12% by weight, more preferably from about 0.5% to about 5% by weight.

Examples of additional herbicidal active ingredients that may be included in the herbicidal compositions include, without limitation, water-soluble forms of phenoxy herbicides such as (2,4-dichlorophenoxy)acetic acid (2,4-D), 4-(2,4-dichlorophenoxy)butanoic acid (2,4-DB) and (4-chloro-2-methylphoenoxy)acetic acid (MCPA), as well as dicamba, diquat bromide, glufosinate, imazapic, imazapyr, imazethapyr, triclopyr and mixtures thereof. Additional herbicidal active ingredients also include forms of these herbicides that are not readily water-soluble (e.g., an ester form of a phenoxy herbicide), that are coupled into the aqueous herbicidal composition by inclusion of a sufficient quantity of an appropriate surfactant. In addition, the compositions of the present invention may include finely-divided, water-insoluble herbicides, for example, triazines, substituted ureas (e.g., diuron), sulfonylureas, diphenyl ethers, dinitroanilines, pryidines, oxyfluorfen, oryzalin and the like. Additional herbicidal active ingredient(s) in an RTU formulation are present in an agriculturally useful concentration that will vary depending on the particular additional herbicide(s) selected for inclusion and is readily determined by those skilled in the art.

The herbicidal compositions may further comprise other conventional adjuvants, excipients or additives known to those skilled in the art. These other additives or ingredients may be introduced into the compositions of the present invention to provide or improve certain desired properties or characteristics of the formulated product. Hence, the herbicidal composition may further comprise one or more additional ingredients selected from, without limitation, foam-moderating agents, preservatives or anti-microbials, antifreeze agents, solubility-enhancing agents, dyes, pH adjusters and thickening agents.

Suitable foam-moderating agents include silicone-based compositions. An example of a foam-moderating agent for RTU compositions is SAG-10, available from GE Silicones Corporation (Wilton, Conn.). The amount of foam-moderating agent optionally employed is that which is sufficient to inhibit and/or reduce an amount of foam that may otherwise be formed during the process of preparing and containerizing the formulation and/or use thereof to a desired and satisfactory level. Generally, in the case of RTU compositions, the concentration of foam-moderating agent is in the range from about 0.001% up to about 0.05% by weight of the composition, and typically from about 0.01% to about 0.03% by weight of the composition, although greater or lesser amounts may be employed.

The compositions may also comprise a preservative such as PROXEL GXL containing 1,2-benzisothiazolin-3-one (CAS No. 2634-33-5) available from Avecia, Inc. (Wilmington, Del.), DOWICIL 150 containing cis-1-(3-chloroallyl)-3, 5,7-triaza-1-azoniaadmatane chloride (CAS No. 051229-78-8) available from Dow Chemical Company (Midland, Mich.), NIPACIDE BIT20DPG containing benzisothiazolinone available from Clariant Corporation (Greensboro, N.C.), LEGEND MK anti-microbial biocide available from Rohm and Haas Co. (Philadelphia, Pa.), sorbic acid, mixtures thereof and the like in the range of from about 0.01% to about 0.2% by weight, preferably about 0.1% by weight of the RTU composition.

Suitable antifreeze agents include ethylene glycol and propylene glycol and generally may be present at a concentration of from about 0.1% to about 10% by weight of the RTU composition. Antifreeze agents assist in lowering the freezing point of aqueous solutions and maintaining solubility of the components of the composition such that components do not crystallize or precipitate during cycles of freezing and thawing.

Although the RTU compositions of the present invention generally show good overall stability and viscosity properties without the addition of any further additives, the addition of a solubility-enhancing agent (also commonly referred to as a cloud point enhancer or stabilizer) may significantly improve the properties of the formulations. Solubility-enhancing agents include polymer derivatives of ethylene glycol and propylene glycol (e.g., 200-1200 average molecular weight), glycerol, sugars, mixtures thereof and the like in amounts up to about 10%, preferably from about 0.05 to about 10% by weight, more preferably from about 0.1 to about 1% by weight of the RTU composition.

The herbicidal RTU compositions of the present invention can be readily prepared by simple mixing of the various components and optional ingredients in the desired quantities using a mechanical stirrer or any other suitable container or device producing the necessary amount of agitation or circulation to thoroughly mix the ingredients. The order of addition of the starting materials is not critical. For example, an herbicidal RTU composition may be formulated by first dissolving ammonium sulfate or other optional inorganic ammonium salt in water, adding the glyphosate component and optional surfactant component, followed by addition of potassium hydroxide or other suitable strong base and then addition of the fatty acid component. Although no particular mixing or formulating technique is required, general reference may be made to the formulation preparation process disclosed in U.S. Pat. No. 5,994,269 (Bugg, et al.), the disclosure of which is incorporated herein by reference.

In the practice of the present invention, the pH of the herbicidal composition is preferably controlled in order to obtain a storage stable formulation and one that effectively provides the desired fast developing symptomology. More particularly, in some embodiments, the final pH of the herbicidal RTU composition is preferably controlled in the range of from about 7.1 to about 7.6. If the pH of the final composition is below about 7.1, the fatty acid component may tend to separate from the composition upon standing and it may be necessary for the user to shake or agitate the composition to obtain a uniform solution to spray. However, if the final pH is greater than about 7.6, the development of symptoms in treated plants may be undesirably delayed. Accordingly, there is a balance to be achieved between these two considerations. In accordance with a more preferred embodiment of the invention, the final pH of the RTU composition is controlled in the range of from about 7.2 to about 7.5, even more preferably, from about 7.25 to about 7.4 and especially at about 7.3.

However, in accordance with some embodiments of the present invention, it has been discovered that the adverse effect of higher pH on early development of symptomology discussed above is substantially diminished if the herbicidal composition includes an inorganic ammonium salt such as ammonium sulfate, preferably in combination with a nonionic surfactant such as an alkoxylated nonaromatic alcohol. Hence, in such an embodiment, suitable results are nevertheless attained when the composition exhibits a final pH in excess of about 7.6, in excess of about 7.7, in excess of about 7.8, in excess of about 7.9 and even up to about 8. Preferably, herbicidal composition including an inorganic ammonium salt in combination with a nonionic surfactant have a pH of from about 7.1 to about 8 and more preferably from about 7.2 to about 7.8. Thus, the combination of an inorganic ammonium salt and nonionic surfactant in the herbicidal compositions of the present invention provides the further advantage of widening the acceptable pH range in the formulated product to provide greater ease and flexibility in the formulation manufacturing process.

If pH adjustment is necessary, it is readily achieved by the addition of pH adjusting base or acidic component such as additional fatty acid or glyphosate component during the formulation preparation process. Suitable bases for pH adjustment include those providing hydroxide in water, preferably an amine or alkali metal or alkaline earth metal hydroxide, and most preferably potassium hydroxide.

The formulation may be filtered (or other equivalent means employed) to remove any insoluble particulate impurities that may be present in some of the ingredients employed (e.g., commercial grades of ammonium sulfate).

The preceding description has focused primarily on aqueous RTU herbicidal compositions provided to the end-user already formulated at the desired dilution and ready for application to the foliage of unwanted plants. However, the herbicidal compositions may alternatively be prepared as concentrates suitable for later dilution in water to obtain a formulation having a composition desired for application. Concentrate formulations permit economy and ease of transportation, for example, from manufacturing site to the site of use.

In the formulation of aqueous concentrate compositions, the concentration of the glyphosate component, fatty acid component and the various optional ingredients are generally higher than as previously described with respect to the RTU formulations. However, as described in greater detail below, it may be advantageous to utilize additional or alternative surfactants, surfactant combinations or solubility-enhancing agents and/or to adjust the relative proportions of the various components of the concentrate in order to attain a stable concentrate solution.

In the preparation of concentrates, a glyphosate component predominantly comprising a salt of N-(phosphonomethyl) glycine, particularly the isopropylammonium salt, ammonium salt, potassium salt or combinations thereof, is preferred in order to take advantage of the high water solubility that facilitate the formulation of highly concentrated herbicidal compositions. Accordingly, there is no practical limitation on the concentration of the glyphosate component in concentrate formulations. The glyphosate component is typically at least about 5% by weight (a.e.), preferably in the range from about 5% to about 25% by weight (a.e.), more preferably from about 10% to about 20% by weight (a.e.) and even more preferably from about 12% to about 18% by weight (a.e.) of the concentrate formulation.

Due to the somewhat limited solubility characteristic of pelargonic acid as well as other fatty acids and derivatives and the optional inorganic ammonium salt at higher concentrations in aqueous formulations, when formulating concentrates, it may be advantageous to employ higher proportions of a surfactant component and/or surfactants or surfactant combinations different from those used in the preparation of RTU formulations and adapted to maintain sufficient solubility of the various components. Examples of the types of suitable surfactants and surfactant combinations that may be used in the surfactant component when formulating concentrate compositions of the present invention include the previously described nonionic surfactant component comprising an alkoxylated nonaromatic alcohol, preferably combined with additional surfactants to enhance stability of the concentrate. Examples of suitable stability enhancing surfactants that may be used either alone or in combination with the nonionic alkoxylated nonaromatic alcohol surfactants include alkyl polyglucosides (APGs), and dialkoxylated quaternary ammonium salt surfactants having the formula:

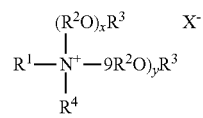

wherein $R^1$ is hydrocarbyl or substituted hydrocarbyl having from 1 to about 30 carbon atoms, $R^2$ in each of the x ($R^2O$) and y ($R^2O$) groups is independently $C_2$-$C_4$ alkylene, $R^3$ is hydrogen, or a linear or branched alkyl group having from 1 to about 4 carbon atoms, $R^4$ is hydrogen or hydrocarbyl or substituted hydrocarbyl having from 1 to about 30 carbon atoms, x and y are independently an average number from 1 to about 40, and $X^-$ is an agronomically acceptable anion. In this context, preferred $R^1$ and $R^4$ hydrocarbyl groups are linear or branched alkyl, linear or branched alkenyl, linear or branched alkynyl, aryl, or aralkyl groups. Preferably, $R^1$ and $R^4$ are independently a linear or branched alkyl or linear or branched alkenyl group having from 1 to about 25 carbon atoms, $R^2$ in each of the x ($R^2O$) and y ($R^2O$) groups is independently $C_2$-$C_4$ alkylene, $R^3$ is hydrogen, methyl or ethyl, and the sum of x and y is an average number from about 2 to about 30. More preferably, $R^1$ and $R^4$ are independently a linear or branched alkyl group having from 1 to about 22 carbon atoms, $R^2$ in each of the x ($R^2O$) and y ($R^2O$) groups is independently ethylene or propylene, $R^3$ is hydrogen or methyl, and the sum of x and y is an average number from about 2 to about 20. Even more preferably, $R^1$ is a linear or branched alkyl group having from about 8 to about 22 carbon atoms and $R^4$ is a linear or branched alkyl group having from 1 to about 22 carbon atoms, $R^2$ in each of the x ($R^2O$) and y ($R^2O$) groups is independently ethylene or propylene, $R^3$ is hydrogen or methyl, and the sum of x and y is an average number from about 2 to about 20. Most preferably, $R^1$ is a linear or branched alkyl group having from about 8 to about 22 carbon atoms and $R^4$ is a linear or branched alkyl group having from 1 to about 6 carbon atoms, $R^2$ in each of the x ($R^2O$) and y ($R^2O$) groups is independently ethylene or propylene, $R^3$ is hydrogen or methyl, and the sum of x and y is an average number from about 2 to about 15, or $R^1$ and $R^4$ are independently a linear or branched alkyl group having from about 8 to about 22 carbon atoms, $R^2$ in each of the x ($R^2O$) and y ($R^2O$) groups is independently ethylene or propylene, $R^3$ is hydrogen or methyl, and the sum of x and y is an average number from about 5 to about 15.

Specific examples of surfactants and surfactant combinations for use in the surfactant component of the concentrate formulations include TOMADOL 1-7 in combination with a dialkoxylated quaternary ammonium salt surfactant such as ETHOQUAD C12 70PG, a PEG 2 coco methyl ammonium chloride from Akzo Nobel (Chicago, Ill.), PEG 5 coco methyl ammonium chloride, PEG 5 tallow methyl ammonium chloride, PEG 5 ditallow ammonium bromide, or PEG 10 ditallow ammonium bromide. In addition, it may be useful to include glycerin, propylene glycol or other glycols when formulating concentrates.

In order to provide a suitably stable concentrate solution, the concentration of the surfactant component is typically at least about 5%, preferably from about 5% to about 50% by weight. The surfactant component and its concentration are preferably selected so as to obtain a "storage stable" concentrate composition. By "storage-stable," it is meant not exhibiting phase separation on exposure to temperatures up to about 50° C., and preferably not forming crystals of glyphosate or salt or other ingredients thereof on exposure to a temperature of about 0° C. for a period of up to about 7 days (i.e., the concentrate composition has a crystallization point of 0° C. or lower). For aqueous solution concentrates, high temperature storage stability is often indicated by a cloud point of about 50° C. or more. Cloud point of a composition is normally determined by heating the composition until the solution becomes cloudy, and then allowing the composition to cool, with agitation, while its temperature is continuously monitored. A temperature reading taken when the solution clears is a measure of cloud point. A cloud point of 50° C. or more is normally considered acceptable for most commercial purposes for a glyphosate concentrate formulation. Ideally the cloud point should be 60° C. or more, and the composition should withstand temperatures as low as about –10° C., preferably as low as about –20° C., more preferably as low as about –30° C., for up to about 7 days without phase separation (i.e., without separation of frozen water or solid insoluble surfactant from the composition) and without crystal growth (even in the presence of seed crystals of the glyphosate salt).

So long as measures are taken to ensure adequate solubility, the concentrates may generally contain at least about 2%, for example from about 2% to about 25% by weight (a.e.) of the fatty acid component and optionally at least about 3%, for example from about 3% to about 18% by weight of an inorganic ammonium salt such as ammonium sulfate. However, in order to maintain sufficient solubility, it may be necessary to adjust the proportions of the fatty acid component and ammonium sulfate as compared to the above-described RTU formulations. In such embodiments, the concentration of the fatty acid component may be no more than about 10% by weight (a.e.), preferably from about 1% to about 5% by weight (a.e.), and the concentration of ammonium sulfate or other inorganic ammonium salt may be no more than about 15% by weight, preferably from about 2% to about 5% by weight. If necessary to attain the desired herbicidal efficacy and early symptomology, the concentration of the fatty acid component and/or inorganic ammonium salt may be increased in the formulation to be applied either contemporaneously with or after dilution of the concentrate. Furthermore, it may be advantageous to entirely omit the optional inorganic ammonium salt from the concentrate composition and, if desired in the formulation to be applied, to add ammonium sulfate or other ammonium salt at the time of dilution of the concentrate.

One example of a concentrate in accordance with the present invention contains about 13 by weight (a.e.) of the glyphosate component as the isopropylammonium salt of N-(phosphonomethyl)glycine, about 3% by weight (a.e.) of pelargonic acid as the fatty acid component about 14% by weight of ETHOQUAD C12 70PG and about 23% by weight of TOMADOL 1-7 as the surfactant component and the remainder water.

The concentrate compositions of the present invention are diluted with a suitable amount of water and optionally augmented as necessary to provide a tank mix having a composition substantially conforming to the RTU compositions of the present invention and ready for spray application to the foliage of unwanted plants.

The present invention is also directed to a method for killing or controlling weeds or other unwanted plants by spraying or otherwise applying a herbicidally effective amount of the RTU or diluted concentrate formulations described herein to the foliage of the plants to be treated. The herbicidal spray compositions included in the present invention can be applied to the foliage of the plants to be treated through any of the appropriate methods that are well known to those having skill in the art. In one embodiment, the RTU composition is packaged in a portable container suitable for hand carry by the user and fitted with an apparatus for manually releasing the composition from the container onto the foliage of the plants to be treated in the form of a spray.

The compositions of the present invention can be used to kill or control the growth of a wide variety of plants. Particularly important annual dicotyledonous plant species include, without limitation, velvetleaf (*Abutilon theophrasti*), pigweed (*Amaranthus* spp.), buttonweed (*Borreria* spp.), oilseed rape, canola, indian mustard, etc. (*Brassica* spp.), commelina (*Commelina* spp.), filaree (*Erodium* spp.), sunflower (*Helianthus* spp.), morningglory (*Ipomoea* spp.), kochia (*Kochia scoparia*), mallow (*Malva* spp.), wild buckwheat, smartweed, etc. (*Polygonum* spp.), purslane (*Portulaca* spp.), Russian thistle (*Salsola* spp.), sida (*Sida* spp.), wild mustard (*Sinapis arvensis*) and cocklebur (*Xanthium* spp.).

Particularly important annual monocotyledonous plant species that may be killed or controlled using the compositions of the present invention include, without limitation, wild oat (*Avena fatua*), carpetgrass (*Axonopus* spp.), downy brome (*Bromus tectorum*), crabgrass (*Digitaria* spp.), barnyardgrass (*Echinochloa crus-galli*), goosegrass (*Eleusine indica*), annual ryegrass (*Lolium multiflorum*), rice (*Oryza sativa*), ottochloa (*Ottochloa nodosa*), bahiagrass (*Paspalum notatum*), canarygrass (*Phalaris* spp.), foxtail (*Setaria* spp.), wheat (*Triticum aestivum*) and corn (*Zea mays*).

Particularly important perennial dicotyledonous plant species for control of which a composition of the invention can be used include, without limitation, mugwort (*Artemisia* spp.), milkweed (*Asclepias* spp.), Canada thistle (*Cirsium arvense*), field bindweed (*Convolvulus arvensis*) and kudzu (*Pueraria* spp.).

Particularly important perennial monocotyledonous plant species for control of which a composition of the invention can be used include, without limitation, brachiaria (*Brachiaria* spp.), bermudagrass (*Cynodon dactylon*), quackgrass (*Elymus repens*), lalang (*Imperata cylindrica*), perennial ryegrass (*Lolium perenne*), guineagrass (*Panicum maximum*), dallisgrass (*Paspalum dilatatum*), reed (*Phragmites* spp.), johnsongrass (*Sorghum halepense*) and cattail (*Typha* spp.).

Other particularly important perennial plant species for control of which a composition of the invention can be used include, without limitation, horsetail (*Equisetum* spp.), bracken (*Pteridium aquilinum*), blackberry (*Rubus* spp.) and gorse (*Ulex europaeus*).

Suitable herbicidally efficacious application or spray rates used in the practice of the present invention will vary depending on the particular composition and concentration of active ingredients, the desired effects, plant species treated, weather and other factors. What constitutes a "desired effect" varies according to the standards and practice of those who investigate, develop, market and use compositions and the selection of application rates that are herbicidally effective for a composition of the invention is within the skill of those skilled in the art.

The herbicidal composition of the present invention is preferably applied to plants at a rate sufficient to give both long term control of plant growth and early visual symptoms of treatment. Typically, the composition is applied at rate sufficient to provide at least about 35%, preferably at least about 50%, more preferably at least about 80% and even more preferably at least about 85% control of a treated plant species as measured by growth reduction or mortality 1 day after treatment, while producing visually apparent phytotoxic effects no later than about 24 hours, preferably no later than about 12 hours and more preferably no later than about 3 hours after treatment. Application rates are classified as a "spray-to-wet" usually expressed as amount of composition per unit area treated (e.g., as gallons/acre or liters m$^2$). In the practice of the present invention, suitable long term control and earlier symptomology are generally achieved by applying the RTU composition at a spray rate of about 145 gallons/acre (0.136 liter/m$^2$).

DEFINITIONS

The term "hydrocarbyl" as used herein describes organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 30 carbon atoms.

The term "substituted hydrocarbyl" as used herein describes hydrocarbyl moieties that are substituted with at least one atom other than carbon, including moieties in which a carbon chain atom is substituted with a hetero atom such as nitrogen, oxygen, silicon, phosphorous, boron, sulfur, or a halogen atom. These substituents include halogen, heterocyclo, alkoxy, alkenoxy, alkynoxy, aryloxy, hydroxy, protected hydroxy, ketal, acyl, acyloxy, nitro, amino, amido, cyano, thiol, acetal, sulfoxide, ester, thioester, ether, thioether, hydroxyalkyl, urea, guanidine, amidine, phosphate, amine oxide, and quaternary ammonium salt.

The term "aryl" as used herein alone or as part of another group denote optionally substituted homocyclic aromatic groups, preferably monocyclic or bicyclic groups containing from 6 to 12 carbons in the ring portion, such as phenyl, biphenyl, naphthyl, substituted phenyl, substituted biphenyl or substituted naphthyl. Phenyl and substituted phenyl are the more preferred aryl.

The term "aralkyl" as used herein denotes a group containing both alkyl and aryl structures such as benzyl.

Unless otherwise indicated, the term "hydroxyalkyl" includes alkyl groups substituted with at least one hydroxy group, e.g., bis(hydroxyalkyl)alkyl, tris(hydroxyalkyl)alkyl and poly(hydroxyalkyl)alkyl groups. Preferred hydroxyalkyl groups include hydroxymethyl (—CH$_2$OH), and hydroxyethyl (—C$_2$H$_4$OH), bis(hydroxy-methyl) methyl (—CH(CH$_2$OH)$_2$), and tris(hydroxymethyl)methyl (—C(CH$_2$OH)$_3$).

The term "cyclic" as used herein alone or as part of another group denotes a group having at least one closed ring, and includes alicyclic, aromatic (arene) and heterocyclic groups.

When a maximum or minimum "average number" is recited herein with reference to a structural feature such as oxyethylene units, it will be understood by those skilled in the art that the integer number of such units in individual molecules in a surfactant preparation typically varies over a range that can include integer numbers greater than the maximum or smaller than the minimum "average number". The presence in a composition of individual surfactant molecules having an integer number of such units outside the stated range in "average number" does not remove the composition from the scope of the present invention, so long as the "average number" is within the stated range and other requirements are met.

Herbicidal effectiveness is one of the biological effects that can be enhanced through this invention. "Herbicidal effectiveness," as used herein, refers to any observable measure of control of plant growth, which can include one or more of the actions of (1) killing, (2) inhibiting growth, reproduction or proliferation, and (3) removing, destroying, or otherwise diminishing the occurrence and activity of plants. The herbicidal effectiveness data set forth herein report "control" as a percentage following a standard procedure in the art which reflects a visual assessment of plant mortality and growth reduction by comparison with untreated plants, made by technicians specially trained to make and record such observations. In all cases, a single technician makes all assessments of percent control within any one experiment or trial.

The following Examples are presented to illustrate the present invention as well as some of the various embodiments of the invention. The invention is not intended to be limited to any of the details in these Examples.

EXAMPLES

The examples will permit better understanding of the invention and its advantages and certain variations of execution. An experimental design was performed to investigate the effect and interactions of components in RTU glyphosate formulations that give fast symptom development on weeds. A series of glyphosate formulations were prepared with varied concentrations of glyphosate salt (e.g., 2% isopropylammonium (IPA) salt of glyphosate (1.48% a.e.)), pelargonic acid, surfactant(s) and inorganic ammonium salt (e.g., ammonium sulfate). The test was to aid in the selection of optimum levels of each component in the formulation and to investigate any interaction between the ingredients.

1. Formulations

In order to assess fast symptomology and long term efficacy, commercial lawn and garden products were compared with experimental aqueous herbicide formulations generated from glyphosate salt (e.g., isopropylammonium salt, GLYPH), pelargonic acid (PA), inorganic ammonium salt (e.g., ammonium sulfate, AMS) and various surfactants (SURF) and additives (OTH) as indicated in Tables 1.1, 1.2, and 1.3. The formulations were tested on a broad spectrum of lawn and garden weeds discussed hereinafter.

TABLE 1.1

Tested Standard Formulations

| CODE | GLYPH wt % ae | PA wt % | AMS wt % | OTHER | OTHER wt % | SURF. 1 | SURF. 1 wt % | SURF. 2 | SURF. 2 wt % |
|---|---|---|---|---|---|---|---|---|---|
| STD 1 | 54.2 | | | OTH9 | 2.9 | | | | |
| STD 2 | 1.4 | | | | | | | | |
| STD 3 | 1.48 | | | | | | | | |
| STD 4 | | | | OTH12 | 22.9 | | | | |
| STD 5 | | | | OTH9 | 0.18 | | | | |
| | | | | OTH11 | 0.06 | | | | |
| STD 6 | 13.3 | | | OTH9 | 0.73 | | | | |
| STD 7 | 37.2 | | | | | | | | |
| 141F1T | 13.3 | | | OTH9 | 0.5 | SUX9T | 9 | SUN2X | 7 |
| 599F5T | 1.48 (K+) | 0 | 0 | OTH9 | 0.055 | SUX9T | 1 | SUN2X | 0.078 |
| 305G4T | 1.48 | 0 | 0 | OTH12 | 1.5 | SUB1 | 7.6 | | |
| | | | | OTH1 | 5 | | | | |
| | | | | OTH2 | 0.1 | | | | |
| | | | | OTH3 | 0.01 | | | | |
| 306H2T | 1.48 | 0 | 0 | OTH12 | 0.75 | SUB1 | 4.2 | | |
| | | | | OTH1 | 3.4 | | | | |
| | | | | OTH2 | 0.1 | | | | |
| | | | | OTH3 | 0.01 | | | | |
| 307L6T | 1.48 | 0 | 0 | OTH12 | 0.5 | SUB1 | 1.2 | SUN6A | 3.6 |
| | | | | OTH1 | 1.2 | | | | |
| | | | | OTH2 | 0.03 | | | | |
| UNTRT | 0 | 0 | 0 | | | | | | |

TABLE 1.2

Tested Experimental Formulations

| Code | GLYPH IPA wt (% a.e.) | PA wt (%) | AMS wt % | OTHER | OTHER wt % | SURF #1 | SURF #1 wt % | SURF #2 | SURF #2 wt % | Stability (cloud pt., crystal. Pt) |
|---|---|---|---|---|---|---|---|---|---|---|
| 295L1V | 1.48 | 2 | | OTH3 | 0.01 | SUB1 | 0.5 | | | Stable |
| | | | | OTH4 | 2.1 | | | | | |
| | | | | OTH5 | 0.1 | | | | | |
| 451A2K | 1.48 | 2 | 2 | OTH3 | 0.01 | SUB1 | 0.5 | | | Stable |
| | | | | OTH4 | 2.1 | | | | | |
| | | | | OTH5 | 0.1 | | | | | |
| 453C7P | 1.48 | 2 | 2 | OTH3 | 0.01 | SUB1 | 0.5 | SUN6A | 1.5 | Stable |
| | | | | OTH4 | 2.1 | | | | | |
| | | | | OTH5 | 0.1 | | | | | |
| 489H1P | 0.74 | 2 | 2 | OTH2 | 0.1 | SUB1 | 0.3 | | | Stable |
| | | | | OTH3 | 0.01 | | | | | |
| | | | | OTH4 | 2.1 | | | | | |
| | | | | OTH13 | 0.016 | | | | | |
| 490K9E | 0.74 | 2 | 2 | OTH3 | 0.01 | SUN6A | 1.5 | | | Stable |
| | | | | OTH4 | 2.1 | | | | | |
| | | | | OTH5 | 0.1 | | | | | |
| | | | | OTH13 | 0.016 | | | | | |
| 998F3S | 1.48 | 2 | | OTH2 | 0.03 | SUB1 | 0.5 | | | Stable |
| | | | | OTH4 | 2.1 | | | | | |
| 578W5Y | 1.42 | 2 | | OTH2 | 0.03 | SUB1 | 0.5 | | | Stable |
| 440A2X | 1.48 | | | OTH2 | 0.03 | SUN6B | 3.6 | | | Layers |
| 440B3Z | 1.48 | | | OTH2 | 0.03 | SUN6C | 3.6 | | | Layers |
| 440C4S | 1.48 | | | OTH2 | 0.03 | SUN6A | 3.6 | | | Stable |
| 440D6H | 1.48 | | | OTH2 | 0.03 | SUN6D | 3.6 | | | Stable |
| 440E7R | 1.48 | | | OTH2 | 0.03 | SUN7A | 3.6 | | | Stable |
| 440F8P | 1.48 | | | OTH2 | 0.03 | SUN7X | 3.6 | | | Stable |

TABLE 1.2-continued

Tested Experimental Formulations

| Code | GLYPH IPA wt (% a.e.) | PA wt (%) | AMS wt % | OTHER | OTHER wt % | SURF #1 | SURF #1 wt % | SURF #2 | SURF #2 wt % | Stability (cloud pt., crystal. Pt) |
|---|---|---|---|---|---|---|---|---|---|---|
| 440G3T | 1.48 | | | OTH2 | 0.03 | SUN7J | 3.6 | | | Stable |
| 440H5C | 1.48 | | | OTH2 | 0.03 | SUN1A | 3.6 | | | Stable |
| 440I2E | 1.48 | | | OTH2 | 0.03 | SUN8T | 3.6 | | | Stable |
| 440J9Q | 1.48 | | | OTH2 | 0.03 | SUN8N | 3.6 | | | Stable |
| 440K1L | 1.48 | | | OTH2 | 0.03 | SUN8M | 3.6 | | | Stable |
| 440L5W | 1.48 | | | OTH2 | 0.03 | SUN8A | 3.6 | | | Stable |
| 440M8D | 1.48 | | | OTH2 | 0.03 | SUN8S | 3.6 | | | Stable |
| 440N6G | 1.48 | | | OTH2 | 0.03 | SUN3X | 3.6 | | | Stable |
| 440O2N | 1.48 | | | OTH2 | 0.03 | SUN3Z | 3.6 | | | Stable |
| 440P4V | 1.48 | | | OTH2 | 0.03 | SUN4Y | 3.6 | | | Stable |
| 440Q7S | 1.48 | | | OTH2 | 0.03 | SUN4G | 3.6 | | | Stable |
| 440R3F | 1.48 | | | OTH2 | 0.03 | SUN2V | 3.6 | | | Stable |
| 441A9S | 1.48 | 2 | | OTH2 OTH4 | 0.03 2.1 | SUN6B | 3.6 | | | Layers |
| 441B4W | 1.48 | 2 | | OTH2 OTH4 | 0.03 2.1 | SUN6C | 3.6 | | | Layers |
| 441C2X | 1.48 | 2 | | OTH2 OTH4 | 0.03 2.1 | SUN6A | 3.6 | | | Stable |
| 441D5C | 1.48 | 2 | | OTH2 OTH4 | 0.03 2.1 | SUN6D | 3.6 | | | Stable |
| 441E8S | 1.48 | 2 | | OTH2 OTH4 | 0.03 2.1 | SUN7A | 3.6 | | | Stable |
| 441F6N | 1.48 | 2 | | OTH2 OTH4 | 0.03 2.1 | SUN7X | 3.6 | | | Stable |
| 441G1R | 1.48 | 2 | | OTH2 OTH4 | 0.03 2.1 | SUN7J | 3.6 | | | Stable |
| 441H7T | 1.48 | 2 | | OTH2 OTH4 | 0.03 2.1 | SUN1A | 3.6 | | | Stable |
| 441I2J | 1.48 | 2 | | OTH2 OTH4 | 0.03 2.1 | SUN8T | 3.6 | | | Stable |
| 441J3S | 1.48 | 2 | | OTH2 OTH4 | 0.03 2.1 | SUN8N | 3.6 | | | Stable |
| 441K7H | 1.48 | 2 | | OTH2 OTH4 | 0.03 2.1 | SUN8M | 3.6 | | | Stable |
| 441L2W | 1.48 | 2 | | OTH2 OTH4 | 0.03 2.1 | SUN8A | 3.6 | | | Stable |
| 441M3D | 1.48 | 2 | | OTH2 OTH4 | 0.03 2.1 | SUN8S | 3.6 | | | Stable |
| 441N9H | 1.48 | 2 | | OTH2 OTH4 | 0.03 2.1 | SUN3X | 3.6 | | | Stable |
| 441O6S | 1.48 | 2 | | OTH2 OTH4 | 0.03 2.1 | SUN3Z | 3.6 | | | Stable |
| 441P4J | 1.48 | 2 | | OTH2 OTH4 | 0.03 2.1 | SUN4Y | 3.6 | | | Stable |
| 441Q5S | 1.48 | 2 | | OTH2 OTH4 | 0.03 2.1 | SUN4G | 3.6 | | | Stable |
| 441R3P | 1.48 | 2 | | OTH2 OTH4 | 0.03 2.1 | SUN2V | 3.6 | | | Stable |
| 433S5C | 1.48 | 2 | | OTH2 OTH4 | 0.1 2.1 | SUN6A | 2.5 | SUB1 | 0.5 | Stable |
| 469A1T | 1.48 | 2 | 1 | OTH2 OTH4 | 0.1 2.1 | SUN6A | 2.5 | SUB1 | 0.5 | Stable |
| 469B8T | 1.48 | 1 | 2 | OTH2 OTH4 | 0.1 1.1 | SUN6A | 3.5 | | | Stable |
| 480C5X | 1.48 | 2 | 1 | OTH2 OTH4 | 0.1 2.1 | SUN6A | 2.5 | | | Stable |
| 483D2T | 1.48 | 2 | 2 | OTH2 OTH4 | 0.1 2.1 | SUN6A | 3.5 | SUB1 | 0.5 | Stable |
| 495G6A | 1.48 | | 2 | OTH2 | 0.1 | SUN6A | 2.5 | | | Stable |
| 475B6Y | 1.48 | 2 | 2 | OTH2 OTH4 | 0.1 2.1 | SUN6A | 1.5 | | | Stable |
| 476K3W | 1.48 | 1 | 2 | OTH2 OTH4 | 0.1 1.1 | SUN6A | 1.5 | | | Stable |
| 513U9D | 1.48 | | 1 | OTH2 | 0.1 | SUN6A | 3.5 | | | Stable |
| 471C9T | 1.48 | 2 | 1 | OTH2 OTH4 | 0.1 2.1 | SUN6A | 3.5 | SUB1 | 0.5 | Stable |
| 471D3T | 1.48 | | | OTH2 | 0.1 | SUN6A | 1.5 | SUB1 | 0.5 | Stable |
| 474E7T | 1.48 | | | OTH2 | 0.1 | SUN6A | 3.5 | SUB1 | 0.5 | Stable |
| 420S8C | 1.48 | | 1 | OTH2 | 0.1 | SUN6A | 2.5 | SUB1 | 0.5 | Stable |
| 435W6E | 1.48 | 1 | 2 | OTH2 OTH4 | 0.1 1.1 | SUN6A | 1.5 | SUB1 | 0.5 | Stable |
| 421L5N | 1.48 | | 2 | OTH2 | 0.1 | SUN6A | 3.5 | | | Stable |
| 525R9B | 1.48 | 1 | | OTH2 OTH4 | 0.1 1.1 | SUN6A | 1.5 | SUB1 | 0.5 | Stable |

TABLE 1.2-continued

Tested Experimental Formulations

| Code | GLYPH IPA wt (% a.e.) | PA wt (%) | AMS wt % | OTHER | OTHER wt % | SURF #1 | SURF #1 wt % | SURF #2 | SURF #2 wt % | Stability (cloud pt., crystal. Pt) |
|---|---|---|---|---|---|---|---|---|---|---|
| 515N3B | 1.48 | 2 | 1 | OTH2 | 0.1 | SUN6A | 1.5 | SUB1 | 0.5 | Stable |
|  |  |  |  | OTH4 | 2.1 |  |  |  |  |  |
| 520C4X | 1.48 | 2 |  | OTH2 | 0.1 | SUN6A | 3.5 |  |  | Stable |
|  |  |  |  | OTH4 | 2.1 |  |  |  |  |  |
| 520W9S | 1.48 | 1 | 1 | OTH2 | 0.1 | SUN6A | 3.5 | SUB1 | 0.5 | Stable |
|  |  |  |  | OTH4 | 1.1 |  |  |  |  |  |
| 345R6C | 1.48 |  |  | OTH2 | 0.1 | SUN6A | 2.5 |  |  | Stable |
| 350F1L | 1.48 | 1 | 2 | OTH2 | 0.1 | SUN6A | 2.5 | SUB1 | 0.5 | Stable |
|  |  |  |  | OTH4 | 1.1 |  |  |  |  |  |
| 235W9D | 1.48 | 2 |  | OTH2 | 0.1 | SUN6A | 1.5 |  |  | Stable |
|  |  |  |  | OTH4 | 2.1 |  |  |  |  |  |
| 240S8G | 1.48 | 2 | 2 | OTH2 | 0.1 | SUN6A | 2.5 |  |  | Stable |
|  |  |  |  | OTH4 | 2.1 |  |  |  |  |  |
| 240D3F | 1.48 | 2 | 1 | OTH2 | 0.1 | SUN6A | 2.5 |  |  | Stable |
|  |  |  |  | OTH4 | 2.1 |  |  |  |  |  |
| 675W3T | 1.48 | 1 | 2 | OTH2 | 0.1 | SUN6A | 1.5 |  |  | Stable |
|  |  |  |  | OTH4 | 1.1 |  |  |  |  |  |
| 245M9S | 1.48 | 2 |  | OTH4 | 2.1 | SUN6A | 2.5 |  |  | Stable |
| 737F2S | 0.72 | 1 | AMN 2.4 | OTH2 | 0.03 | SUB2 | 0.15 |  |  | Stable |
|  |  |  |  | OTH3 | 0.01 |  |  |  |  |  |
|  |  |  |  | OTH4 | 1.1 |  |  |  |  |  |
| 490W1M | 1.45 | 2 | 2 | OTH1 | 0.66 | SUN6A | 3.6 |  |  | Stable |
|  |  |  |  | OTH2 | 0.03 |  |  |  |  |  |
|  |  |  |  | OTH4 | 2.1 |  |  |  |  |  |
| 735T2H | 1.45 | 2 | 2 | OTH1 | 0.66 | SUN6A | 3.6 | SUB1 | 0.5 | Stable |
|  |  |  |  | OTH2 | 0.03 |  |  |  |  |  |
|  |  |  |  | OTH4 | 1 |  |  |  |  |  |
| 740M5C | 1.45 | 1 | 2 | OTH1 | 0.66 | SUB1 | 0.5 |  |  | Stable |
|  |  |  |  | OTH2 | 0.03 |  |  |  |  |  |
|  |  |  |  | OTH4 | 1 |  |  |  |  |  |
| 750R8X | 1.45 | 2 |  | OTH1 | 0.66 | SUN9X | 3.6 |  |  | Stable |
|  |  |  |  | OTH2 | 0.03 |  |  |  |  |  |
|  |  |  |  | OTH4 | 2.1 |  |  |  |  |  |
| 920M2V | 1.45 | 2 | 2 | OTH1 | 0.66 | SUN9X | 3.6 | SUB1 | 0.5 | Stable |
|  |  |  |  | OTH2 | 0.03 |  |  |  |  |  |
|  |  |  |  | OTH4 | 2.1 |  |  |  |  |  |
| 308J8T | 1.48 |  |  | OTH1 | 5 |  |  | SUB1 | 7.6 | Stable |
|  |  |  |  | OTH2 | 0.1 |  |  |  |  |  |
| 322K9T | 1.45 |  | 2 | OTH1 | 0.66 | SUN6A | 3.6 |  |  | Stable |
|  |  |  |  | OTH2 | 0.03 |  |  |  |  |  |
|  |  |  |  | OTH6 | 0.01 |  |  |  |  |  |
| 022K8T | 1.48 | 2 | 2 | OTH2 | 0.1 | SUB1 | 0.5 | SUN6A | 2.5 | Stable |
|  |  |  |  | OTH4 | 1 |  |  |  |  |  |
| 452B9X | 1.48 | 1 | 2 | OTH2 | 0.1 | SUN6A | 2.5 |  |  | Stable |
|  |  |  |  | OTH3 | 0.01 |  |  |  |  |  |
|  |  |  |  | OTH4 | 2 |  |  |  |  |  |
| 454D4K | 1.48 | 2 | 1 | OTH2 | 0.1 | SUN6A | 2.5 |  |  | Stable |
|  |  |  |  | OTH3 | 0.01 |  |  |  |  |  |
|  |  |  |  | OTH4 | 2.6 |  |  |  |  |  |
| 455E8S | 1.48 | 2 |  | OTH2 | 0.1 | SUN6A | 3.5 |  |  | Stable |
|  |  |  |  | OTH3 | 0.01 |  |  |  |  |  |
|  |  |  |  | OTH4 | 2.6 |  |  |  |  |  |
| 456F6H | 1.48 | 1 |  | OTH2 | 0.1 | SUN6A | 3.5 |  |  | Stable |
|  |  |  |  | OTH3 | 0.01 |  |  |  |  |  |
|  |  |  |  | OTH4 | 2 |  |  |  |  |  |
| 457G1T | 1.48 | 2 | 0.75 | OTH2 | 0.1 | SUN6A | 2 |  |  | Stable |
|  |  |  |  | OTH3 | 0.05 |  |  |  |  |  |
|  |  |  |  | OTH4 | 0.5 |  |  |  |  |  |
| 458W3S | 1.48 | 2 | 2 | OTH2 | 0.1 | SUB1 | 0.5 | SUN6A | 3.5 | Stable |
|  |  |  |  | OTH3 | 0.05 |  |  |  |  |  |
|  |  |  |  | OTH4 | 2 |  |  |  |  |  |

TABLE 1.3

Standards, Surfactants, and other Additives

STANDARDS

| CODE | LABEL |
|---|---|
| STD 1 | ROUNDUP QUICK PRO |
| STD 2 | ROUNDUP FAST-ACT FOAM |
| STD 3 | STATESMAN RTU |
| STD 4 | BARRIER H |
| STD 5 | SPECTRACIDE RTU |
| STD 6 | ROUNDUP CONC PLUS |
| STD 7 | ROUNDUP SUPER CONC |

| CODE | LABEL | COMPONENTS |
|---|---|---|
| | | SURFACTANTS |
| SUB1 | 112D5Y | Surfactant blend; Tallowamine ethoxylate (~10 EO) and alkylethoxylate phosphate ester formulations. |
| SUB2 | 117P3W | Etheramine surfactant (isotridecyloxypropylamine EO5). |
| SUB3 | 818I7M | Surfactant blend of Tallowamine ethoxylate (15EO)] in Polyethylene glycol & Ethylene glycol |
| SUC1A | AGRISOL A-250HC | Blend of 2EO Methylcocoammonium quat, 10EO isotridecyl alcohol in Dipropylene glycol (DPG) |
| SUN1A | TRITON X-100 | 9-10EO Octylphenol |
| SUN2V | WICONOL TD-1407 | 20EO Tallowamine |
| SUN3X | MAKON 6 | 6EO Nonylphenol |
| SUN3Z | MAKON 12 | 12EO Nonylphenol |
| SUN4G | DD-5 | 5EO Dodecylphenol |
| SUN4Y | DD-10 | 10EO Dodecylphenol |
| SUN5H | C-6101 | 50% 10.5EO Tallowamine in 50% Dipropylene glycol (DPG) |
| SUN6C | TOMADOL 1-3 | Linear alcohol ethoxylate 3EO Undecyl alcohol |
| SUN6B | TOMADOL 1-5 | Linear alcohol ethoxylate 5EO Undecyl alcohol |
| SUN6A | TOMADOL 1-7 | Linear alcohol ethoxylate 7EO Undecyl alcohol |
| SUN6D | TOMADOL 1-9 | Linear alcohol ethoxylate 9EO Undecyl alcohol |
| SUN7A | TOMADOL 25-3 | Linear C12-15 alcohol with ~3 moles (average) EO ethylene oxide. |
| SUN7X | TOMADOL 25-7 | Linear C12-15 alcohol with 7 moles (average) EO |
| SUN7J | TOMADOL 25-9 | Linear C12-15 alcohol with 9 moles (average) EO |
| SUN8A | SURFONIC L12-7 | Low foaming C11-12 linear alcohol alkoxylate (EO/PO); degree of alkoxylation = 7 |
| SUN8M | SURFONIC L24-6.5 | Low foaming C12-14 linear alcohol alkoxylate (EO/PO); degree of alkoxylation = 6.5 |
| SUN8S | SURFONIC L24-7 | Low foaming C12-14 linear alcohol alkoxylate (EO/PO); degree of alkoxylation = 7 |
| SUN8N | SURFONIC L24-9 | Low foaming C12-14 linear alcohol alkoxylate (EO/PO); degree of alkoxylation = 9 |
| SUN8T | SURFONIC L24-12 | Low foaming C12-14 linear alcohol alkoxylate (EO/PO); degree of alkoxylation = 12 |
| SUN9X | TERGITOL 15-S-9 | C11-C15 linear secondary alcohol ethoxylate; 9 EO |
| SUX9T | SILWET 800 | Organosilicone surfactant |
| SUN2X | TRIMETHYL COCOAMINE | |
| | | OTHER ADDITIVES |
| OTH1 | PROPYLENE GLYCOL | Solvent; antifreeze |
| OTH2 | PROXEL GXL | Preservative |
| OTH3 | SAG 10 | Antifoam |
| OTH4 | KOH | Base |
| OTH5 | NIPACIDE BIT20DPG | Preservative |
| OTH6 | SHIN ETSU KM90 | Antifoam |
| OTH7 | LEGEND MK | Preservative |
| OTH8 | AMMONIUM NITRATE | Salt |
| OTH9 | DIQUAT DIBROMIDE | Herbicide |
| OTH10 | GLUFOSINATE AMMONIUM | Herbicide |
| OTH11 | FLUAZIFOP-p-BUTYL | Herbicide |
| OTH12 | CITRONELLOL | |
| OTH13 | IMAZAPIC | Herbicide |

2. Stability Test and Results

Various formulations were maintained at constant temperature for a fixed period and monitored for changes in color, homogeneity and appearance after thawing. The formulations were also cycled through temperature extremes (i.e., at low temperatures of −20° C. and −5° C. for the fixed period then raised to the higher temperatures of 20° C. and 5° C., respectively) and changes monitored. Results are presented in Table 1.2 above.

3. Greenhouse Test and Results

Standard post emergence herbicide application procedures were used, as described below, to formulations listed in Tables 1.1-1.3.

Seeds of the plant species, white clover (TRFRE), tall fescue (FESAR), large crabgrass (DIGSA) and common purslane (POROL), were planted in 3.5 in square pots in a soil mix which was previously steam sterilized and prefertilized with a 14-28-14 N-P-K slow release fertilizer at a concentration of 3.53 g/L. The pots were placed in a greenhouse with sub-irrigation. About one week after emergence, seedlings were thinned as needed, including removal of any unhealthy or abnormal plants, to create a uniform series of test pots.

The plants were maintained for the duration of the test in the greenhouse where they received a minimum of 14 hours of light per day. If natural light was insufficient to achieve the daily requirement, artificial light with an intensity of approximately 475 microeinsteins was used to make up the difference. Exposure temperatures averaged about 27° C. during the day and about 21° C. during the night. Plants were sub-irrigated throughout the test to ensure adequate soil moisture levels.

Pots were assigned to different treatments in a randomized experimental design with 3 replications. A set of pots was left untreated as a reference against which effects of the treatments could later be evaluated. Application of tested formulations was made by spraying with a lawn and garden 24-oz trigger sprayer fitted with an RTU pump applicator calibrated to deliver a spray volume of 1348 liters per hectare (1/ha). After treatment, pots were returned to the greenhouse until ready for evaluation. Treatments were made using dilute aqueous compositions.

For evaluation of herbicidal effectiveness, all plants in the test were examined by a single practiced technician, who recorded percent control, a visual measurement of the effectiveness of each treatment by comparison with untreated plants. Control of 0% indicates no effect, and control of 100% indicates that all of the plants are completely dead. Control of 85% or more is in most cases considered acceptable for normal herbicide use; however in greenhouse tests such as those for the examples it is normal to apply compositions at rates which give less than 85% control, as this makes it easier to discriminate among compositions having different levels of effectiveness. The reported % control values represent the average for all replicates of each treatment.

The results of the Greenhouse Tests are summarized in Tables 3a-3c. The data is reported as % control (treated vs. untreated) at 1, 3, 5, 7, 14 and 21 DAT (days after treatment) for each species in Table 3a. Similarly the data is reported at 1, 3, 7, 14 and 21 DAT in Tables 3b and 3c.

TABLE 3a

Results of Greenhouse Efficacy Study of Experimental and Standard Glyphosate Formulations on Lawn & Garden Weed Spectrum

| CODE | TRFRE 1, 3, 5, 7, 14, 21 DAT | FESAR 1, 3, 5, 7, 14, 21 DAT | DIGSA 1, 3, 5, 7, 14, 21 DAT | SPECIES AVE. 1, 3, 5, 7, 14, 21 DAT |
|---|---|---|---|---|
| 307F1S | 53, 83, 88, 90, 87, 83 | 25, 68, 79, 80, 85, 98 | 55, 58, 72, 67, 72, 87 | 44, 70, 80, 79, 81, 89 |
| STD 1 | 60, 89, 94, 97, 96, 93 | 47, 85, 91, 93, 93, 99 | 65, 80, 88, 93, 96, 95 | 57, 85, 91, 94, 95, 95 |
| STD 2 | 68, 68, 67, 67, 64, 75 | 70, 89, 98, 97, 98, 99 | 67, 78, 80, 82, 87, 99 | 68, 79, 82, 82, 83, 91 |
| STD 3 | 78, 81, 90, 89, 87, 95 | 27, 73, 83, 88, 95, 100 | 72, 77, 79, 76, 80, 88 | 59, 77, 84, 85, 87, 94 |
| 737F2S | 72, 72, 77, 78, 73, 70 | 47, 68, 74, 74, 85, 99 | 53, 65, 77, 82, 87, 92 | 57, 68, 76, 78, 81, 87 |
| 998F3S | 76, 77, 82, 83, 80, 92 | 67, 87, 91, 89, 93, 98 | 48, 63, 75, 76, 92, 98 | 64, 76, 83, 83, 88, 96 |
| 141F1T | 52, 87, 86, 91, 91, 87 | 25, 77, 83, 92, 96, 100 | 50, 72, 82, 85, 96, 93 | 43, 79, 84, 89, 94, 93 |
| STD 4 | 85, 84, 84, 79, 65, 25 | 80, 78, 73, 69, 62, 27 | 78, 82, 72, 62, 52, 27 | 81, 81, 76, 70, 59, 26 |
| 469A1T | 84, 87, 96, 94, 92, 93 | 83, 89, 93, 89, 89, 98 | 60, 70, 77, 81, 90, 97 | 76, 82, 88, 88, 90, 96 |
| 469B8T | 73, 78, 84, 82, 82, 85 | 79, 94, 98, 97, 99, 100 | 75, 84, 88, 93, 97, 100 | 76, 85, 90, 91, 93, 95 |
| 471C9T | 78, 83, 91, 90, 89, 95 | 58, 83, 90, 91, 93, 99 | 68, 80, 83, 82, 91, 100 | 68, 82, 88, 88, 91, 98 |
| 471D3T | 83, 87, 88, 88, 86, 83 | 70, 84, 92, 92, 97, 97 | 60, 81, 85, 88, 88, 98 | 71, 84, 88, 89, 90, 93 |
| 474E7T | 83, 86, 86, 89, 89, 90 | 57, 76, 82, 84, 84, 92 | 62, 77, 80, 84, 93, 100 | 67, 80, 83, 86, 89, 94 |
| 599F5T | 68, 92, 99, 99, 99, 99 | 22, 78, 95, 95, 95, 98 | 50, 73, 81, 85, 89, 85 | 47, 81, 92, 93, 94, 94 |
| 305G4T | 62, 80, 87, 87, 85, 90 | 10, 42, 63, 83, 93, 99 | 30, 47, 70, 78, 93, 100 | 34, 56, 73, 83, 90, 96 |
| 306H2T | 53, 76, 86, 87, 89, 94 | 4, 15, 45, 75, 93, 99 | 25, 47, 73, 87, 100, 100 | 27, 46, 68, 83, 94, 98 |
| 307L6T | 70, 78, 87, 86, 84, 83 | 23, 72, 78, 83, 87, 100 | 60, 70, 82, 83, 95, 99 | 51, 73, 83, 84, 89, 94 |
| 308J8T | 48, 77, 87, 91, 99, 99 | 7, 12, 40, 63, 83, 99 | 15, 30, 55, 80, 100, 100 | 23, 40, 61, 78, 94, 100 |
| 322K9T | 88, 93, 99, 99, 100, 99 | 12, 50, 65, 78, 88, 99 | 58, 70, 70, 73, 82, 98 | 53, 71, 78, 84, 90, 99 |

Discussion:

This test demonstrates that the formulation with 1% PA and 2.4% ammonium nitrate (737F2S) does not perform as well as to fast symptom development, particularly on tall fescue, as the formulations that contain 2% PA or 1% PA and 2% AMS.

The data also shows that ammonium sulfate does not increase the fast symptom development on grass species (crab and tall fescue) when the formulation only contains the NIS surfactant (STD 3 vs. 322K9T). The data also shows that an iso-alcohol surfactant gives equivalent fast symptom development when compared to a completely linear alcohol when combined with PA+/-AMS (comparing 305G4T & 306H2T to 474E7T). Also in this trial, 308J8T which contains 7.6% of the proprietary blend (alkylphosphate ester plus tallowamine ethoxylate surfactant) does not show equivalent fast symptom development to the PA+/-NIS+/-AMS formulations.

TABLE 3b

Results of Greenhouse Efficacy Study of Experimental Glyphosate Formulations containing various Nonionic Surfactants with or without Pelargonic Acid on Lawn & Garden Weed Spectrum

| CODE | DIGSA 1, 3, 7, 14, 21 DAT | POROL 1, 3, 7, 14, 21 DAT | FESAR 1, 3, 7, 14, 21 DAT | TRFRE 1, 3, 7, 14, 21 DAT |
|---|---|---|---|---|
| 440A2X | 72, 82, 96, 99, 100 | 70, 82, 92, 91, 93 | 65, 80, 89, 89, 92 | 85, 93, 93, 92, 90 |
| 440B3Z | 73, 81, 94, 98, 100 | 73, 87, 94, 94, 98 | 40, 65, 78, 85, 84 | 83, 92, 93, 89, 86 |
| 440C4S | 75, 78, 91, 93, 99 | 73, 85, 95, 97, 99 | 50, 58, 77, 86, 96 | 82, 88, 93, 93, 91 |
| 440D6H | 62, 65, 72, 90, 100 | 64, 77, 84, 82, 82 | 20, 33, 47, 72, 90 | 70, 80, 90, 86, 84 |
| 440E7R | 67, 83, 87, 97, 99 | 55, 67, 81, 87, 93 | 18, 35, 58, 73, 95 | 75, 77, 97, 98, 99 |
| 440F8P | 60, 75, 92, 97, 100 | 45, 60, 83, 85, 98 | 7, 37, 48, 72, 96 | 65, 70, 90, 91, 94 |
| 440G3T | 58, 68, 73, 87, 100 | 40, 63, 85, 90, 98 | 4, 22, 38, 65, 100 | 60, 70, 96, 98, 100 |
| 440H5C | 40, 55, 68, 99, 100 | 25, 43, 82, 97, 100 | 5, 20, 33, 72, 100 | 70, 75, 97, 98, 100 |
| 440I2E | 55, 62, 67, 85, 100 | 42, 70, 84, 89, 99 | 5, 15, 30, 67, 90 | 65, 65, 82, 85, 85 |
| 440J9Q | 67, 68, 73, 88, 100 | 53, 76, 88, 88, 97 | 12, 30, 53, 71, 93 | 68, 73, 88, 92, 92 |
| 440K1L | 63, 82, 90, 93, 100 | 60, 75, 83, 88, 96 | 20, 47, 53, 73, 86 | 73, 73, 82, 90, 90 |
| 440L5W | 75, 87, 96, 94, 100 | 75, 86, 93, 94, 97 | 43, 67, 72, 78, 91 | 82, 87, 89, 95, 95 |
| 440M8D | 68, 82, 93, 95, 100 | 63, 77, 84, 91, 99 | 15, 33, 40, 72, 100 | 73, 75, 93, 99, 99 |
| 440N6G | 45, 65, 75, 100, 100 | 33, 42, 75, 93, 100 | 5, 13, 25, 75, 100 | 62, 68, 90, 97, 99 |
| 440O2N | 47, 73, 78, 96, 100 | 30, 57, 82, 94, 99 | 10, 25, 48, 77, 100 | 65, 70, 83, 95, 98 |
| 440P4V | 22, 45, 62, 100, 100 | 5, 20, 69, 100, 100 | 5, 10, 22, 75, 100 | 50, 60, 83, 98, 99 |
| 440Q7S | 20, 45, 65, 98, 100 | 10, 27, 67, 95, 100 | 3, 5, 17, 65, 100 | 38, 56, 91, 100, 100 |
| 440R3F | 45, 55, 68, 88, 100 | 17, 53, 80, 98, 100 | 4, 15, 23, 63, 100 | 45, 55, 82, 93, 99 |
| 441A9S | 82, 93, 99, 99, 99 | 90, 96, 100, 100, 100 | 78, 87, 94, 94, 95 | 93, 96, 98, 99, 100 |
| 441B4W | 80, 85, 96, 96, 97 | 86, 92, 100, 100, 100 | 78, 87, 93, 94, 94 | 92, 98, 98, 99, 99 |
| 441C2X | 82, 92, 98, 99, 100 | 80, 90, 99, 99, 100 | 67, 84, 90, 95, 100 | 96, 99, 100, 100, 100 |
| 441D5C | 78, 85, 89, 94, 96 | 82, 92, 98, 99, 100 | 63, 77, 82, 87, 95 | 87, 88, 89, 92, 92 |
| 441E8S | 77, 92, 101, 100, 100 | 90, 94, 99, 100, 100 | 63, 70, 74, 83, 94 | 83, 88, 91, 94, 94 |
| 441F6N | 75, 87, 96, 98, 99 | 88, 95, 97, 99, 99 | 57, 67, 80, 84, 99 | 82, 93, 94, 94, 94 |
| 441G1R | 72, 83, 94, 94, 99 | 74, 88, 93, 96, 100 | 50, 67, 72, 82, 97 | 77, 80, 83, 86, 93 |
| 441H7T | 70, 80, 95, 95, 100 | 52, 67, 88, 99, 100 | 65, 77, 88, 92, 99 | 75, 80, 87, 88, 96 |
| 441I2J | 70, 80, 94, 96, 100 | 78, 90, 95, 97, 100 | 48, 63, 82, 90, 98 | 80, 88, 93, 95, 99 |
| 441J3S | 68, 82, 91, 96, 100 | 85, 93, 98, 99, 100 | 63, 73, 88, 95, 99 | 78, 83, 85, 83, 88 |
| 441K7H | 70, 82, 95, 96, 100 | 75, 87, 97, 98, 100 | 57, 78, 82, 92, 99 | 84, 88, 94, 99, 100 |
| 441L2W | 70, 89, 100, 100, 100 | 80, 92, 99, 100, 100 | 53, 75, 83, 92, 94 | 75, 85, 82, 86, 88 |
| 441M3D | 70, 87, 96, 98, 100 | 90, 96, 100, 100, 100 | 60, 82, 83, 90, 99 | 78, 87, 90, 91, 91 |
| 441N9H | 70, 82, 95, 96, 100 | 63, 74, 84, 92, 99 | 60, 79, 87, 95, 98 | 60, 67, 70, 80, 88 |
| 441O6S | 60, 81, 91, 97, 100 | 32, 60, 91, 99, 100 | 40, 62, 75, 95, 99 | 63, 69, 89, 99, 99 |
| 441P4J | 60, 82, 88, 99, 100 | 38, 65, 82, 94, 99 | 32, 58, 68, 83, 94 | 63, 70, 78, 87, 87 |
| 441Q5S | 62, 78, 83, 96, 99 | 67, 78, 90, 98, 99 | 33, 63, 70, 80, 98 | 75, 80, 88, 94, 94 |

TABLE 3b-continued

Results of Greenhouse Efficacy Study of Experimental Glyphosate Formulations containing various Nonionic Surfactants with or without Pelargonic Acid on Lawn & Garden Weed Spectrum

| CODE | DIGSA 1, 3, 7, 14, 21 DAT | POROL 1, 3, 7, 14, 21 DAT | FESAR 1, 3, 7, 14, 21 DAT | TRFRE 1, 3, 7, 14, 21 DAT |
|---|---|---|---|---|
| 441R3P | 72, 83, 88, 93, 98 | 70, 78, 94, 97, 90 | 62, 70, 72, 75, 91 | 78, 83, 86, 89, 89 |

Discussion:

This test explored the type of nonionic surfactant that would give fast symptom development when applied either with glyphosate alone or in combination with PA.

Note, the formulations that contained the linear (TOMADOL, SURFONIC L) surfactants gave much better 1 DAT symptoms than the alkylphenol type surfactants (TRITON X-100, MAKON 6 or 12, DD 10 or 5) or the highly branched surfactant WITCONOL TD1407 (2,4,6,8 tetramethylnonyl alcohol ethoxylate, EO7). Also demonstrated was the combination of these mostly linear surfactants with pelargonic acid gave in general better fast symptom development than the surfactant alone.

The data also suggests that the $C_{11}EO7$ alcohol may yield the best balance between stability and fast symptomology. As EO level increases from 3-5-7, the EO3 alcohol solution separates into layers at room temperature, the EO5 to a lesser extent separates, while the EO7 and higher containing formulations are homogeneous.

TABLE 3c

Results of Greenhouse Efficacy Study of Experimental Glyphosate Formulations containing Nonionic Surfactants ± Pelargonic Acid ± Ammonium Sulfate on Lawn & Garden Weed Spectrum

| CODE | DIGSA 1, 3, 7, 14, 21 DAT | POROL 1, 3, 7, 14, 21 DAT | FESAR 1, 3, 7, 14, 21 DAT | TRFRE 1, 3, 7, 14, 21 DAT |
|---|---|---|---|---|
| 998F3S non-foam | 40, 73, 89, 95, 98 | 52, 65, 73, 90, 99 | 65, 79, 81, 90, 91 | 66, 71, 72, 83, 98 |
| 998F3S Foaming | 50, 72, 82, 93, 94 | 63, 78, 80, 92, 98 | 67, 81, 83, 94, 98 | 62, 71, 76, 90, 99 |
| STD 2 non-foam | 38, 70, 81, 91, 91 | 70, 72, 76, 89, 96 | 64, 75, 84, 94, 93 | 75, 78, 79, 87, 95 |
| STD 2 foaming | 40, 68, 79, 94, 95 | 65, 80, 83, 96, 99 | 62, 77, 84, 96, 97 | 60, 63, 71, 75, 86 |
| STD 3 | 62, 75, 75, 85, 93 | 69, 80, 85, 92, 94 | 52, 73, 79, 96, 98 | 72, 75, 78, 89, 96 |
| STD 7 | 5, 32, 53, 98, 100 | 7, 42, 65, 88, 100 | 2, 23, 42, 88, 100 | 13, 47, 75, 95, 99 |
| 433S5C | 63, 75, 79, 86, 91 | 85, 94, 98, 98, 99 | 70, 85, 88, 93, 94 | 82, 84, 83, 84, 90 |
| 469A1T | 65, 82, 79, 85, 88 | 85, 92, 99, 99, 100 | 70, 88, 88, 93, 93 | 82, 81, 79, 83, 88 |
| 469B8T | 63, 80, 83, 86, 93 | 83, 93, 97, 98, 99 | 68, 88, 88, 94, 95 | 80, 82, 79, 82, 89 |
| 480C5X | 70, 83, 85, 87, 89 | 80, 91, 98, 99, 100 | 72, 87, 88, 95, 95 | 81, 78, 75, 71, 80 |
| 483D2T | 70, 81, 80, 87, 94 | 79, 92, 96, 99, 98 | 73, 87, 88, 94, 96 | 87, 89, 88, 84, 83 |
| 495G6A | 52, 75, 77, 89, 95 | 69, 87, 84, 90, 90 | 37, 68, 69, 85, 96 | 83, 86, 90, 90, 98 |
| 475B6Y | 69, 79, 79, 84, 91 | 86, 91, 99, 99, 99 | 77, 87, 86, 88, 92 | 83, 84, 82, 84, 86 |
| 476K3W | 58, 70, 76, 86, 90 | 73, 87, 83, 92, 97 | 72, 85, 89, 95, 96 | 75, 78, 81, 91, 96 |
| 513U9D | 48, 65, 70, 86, 90 | 70, 84, 86, 90, 89 | 42, 66, 70, 89, 98 | 72, 82, 82, 84, 93 |
| 471C9T | 65, 75, 75, 83, 88 | 82, 94, 98, 100, 99 | 62, 78, 80, 85, 86 | 77, 78, 80, 84, 89 |
| 471D3T | 32, 42, 60, 96, 99 | 45, 68, 73, 88, 95 | 32, 57, 63, 90, 100 | 63, 75, 75, 75, 95 |
| 474E7T | 55, 65, 72, 87, 93 | 71, 90, 93, 93, 93 | 33, 66, 71, 89, 98 | 63, 69, 65, 71, 82 |
| 420S8C | 55, 65, 72, 88, 96 | 68, 85, 84, 88, 90 | 43, 68, 72, 92, 97 | 72, 75, 74, 74, 80 |
| 435W6E | 60, 67, 72, 87, 95 | 76, 83, 89, 95, 98 | 60, 78, 80, 85, 90 | 78, 81, 82, 79, 89 |
| 421L5N | 55, 73, 75, 89, 95 | 74, 89, 92, 94, 97 | 48, 67, 73, 88, 90 | 77, 79, 79, 78, 86 |
| 525R9B | 60, 74, 77, 86, 89 | 68, 85, 85, 92, 98 | 55, 77, 80, 88, 93 | 74, 79, 79, 79, 85 |
| 515N3B | 70, 85, 86, 89, 96 | 80, 91, 95, 97, 99 | 70, 83, 83, 87, 92 | 87, 89, 85, 85, 87 |
| 520C4X | 65, 80, 80, 84, 85 | 80, 93, 98, 99, 100 | 63, 81, 86, 87, 83 | 82, 83, 83, 82, 87 |
| 520W9S | 63, 80, 83, 87, 95 | 79, 91, 96, 97, 99 | 62, 80, 80, 88, 88 | 81, 88, 87, 85, 89 |
| 345R6C | 48, 79, 80, 90, 97 | 68, 84, 79, 83, 92 | 37, 64, 68, 87, 98 | 80, 83, 80, 80, 83 |
| 350F1L | 58, 68, 72, 86, 89 | 81, 95, 99, 100, 100 | 60, 77, 80, 83, 85 | 80, 93, 90, 94, 95 |
| 235W9D | 63, 78, 79, 87, 85 | 82, 93, 96, 99, 100 | 68, 82, 81, 81, 85 | 83, 83, 84, 74, 86 |
| 240S8G | 67, 77, 76, 82, 83 | 83, 97, 99, 100, 100 | 77, 88, 87, 93, 95 | 82, 83, 78, 78, 83 |
| 240D3F | 68, 72, 70, 78, 82 | 85, 98, 100, 100, 100 | 70, 82, 82, 89, 91 | 83, 88, 85, 81, 83 |
| 675W3T | 40, 60, 65, 93, 98 | 68, 78, 78, 87, 93 | 42, 63, 69, 88, 97 | 75, 84, 89, 94, 98 |
| 245M9S | 63, 77, 75, 83, 83 | 80, 94, 97, 98, 100 | 70, 84, 84, 89, 94 | 80, 86, 83, 80, 84 |

Discussion:

This test explored the efficacy advantage of formulations that contained TOMADOL 1-7 (linear $C_{11}$ alcohol EO7) or NIS Surfactant with and without either pelargonic acid (PA) or ammonium sulfate (AMS). Also in this test, the level of PA and AMS that would give the best overall fast symptom development (1 DAT) was explored. Overall, the treatments containing AMS gave better symptoms than treatments without AMS.

4. Field Study of Experimental and Commercial Glyphosate Formulations

Field studies were conducted using the compositions of the present invention. Compositions were prepared as in Tables 1.1-1.3. Each composition as well as STD5, STD6 and STD7 were applied to the species listed below (Table 4.1) at a rate equivalent to 1348 liters per hectare (l/ha) with % control results reported in Tables 4.2a-4.2e.

Glyphosate formulations were applied post-emergence to all weed targets, generally when they were between about 8 cm and about 30 cm tall, depending on the species and the environmental conditions. Treated plot size was generally 0.92 meters wide and 1.5 meters long. Treatments were applied with a two-gallon ROUNDUP pump up sprayer. Carrier volume was equal to 1348 l/ha. A single Tee-Jet brand tapered flat fan spray tip was used, at an appropriate spray pressure. Experimental design in each study was randomized complete block design with three replications.

Weed control ratings were made by a single practiced technician, who recorded percent control at various time points after treatment. Ratings were based on quantitative visual estimates (0=no control, 100=completely dead, 85% threshold for commercial control). The effect of the formulation on the species in the treated plot was compared to the health and vigor of the species in the untreated buffer area immediately adjacent to the plot. Results are presented in Tables 4.2a-4.2e.

TABLE 4.1

Lawn & Garden Plants evaluated include the following; these are exemplary, but not limiting.

| Bayer Code | Common Name |
|---|---|
| ANOSS | beardgrass, big bluestem sp. (*Andropogon* sp.) |
| ASCLA | milkweed, labriform (*Asclepias labriformis* Jones) |
| CYNDA | bermudagrass (*Cynodon dactylon*) |
| DIORC | Carolina dichondra |
| DIGSA | large crabgrass (*Digitaria sanguinalis*) |
| DIGSO | crabgrass, blanket (*Digitaria serotina* (Walt.) Michx.) |
| EUPCP | dogfenel (*Eupatorium capillifolium* (Lam.) small) |
| FESAR | tall fescue, (*Festuca arundinacea* Schreb); as turf grass |
| FESAW | tall fescue; as weed |
| LIPNO | lippia, mat (*Nodiflora* (L.) Greene) |
| PASDI | dallisgrass (*Paspalum dilatatum*) |
| PASUR | vesseygrass (*Paspalum urvillei* Steud.) |
| PLALA | buckhorn plantain (*Plantago lanceolata*) |
| POAPR | kentucky bluegrass (*Poa pratensis* L.) |
| POEPR | rustweed (*Polypremum procumbens*) |
| POROL | common purslane (*Portulaca oleracea*) |
| TTTTT | total weeds, i.e., all weeds present |
| TAROF | common dandelion (*Taraxacum officinale*) |
| TRFRE | white clover (*Trifolium repens*) |
| TRFPR | red clover (*Trifolium pratense*) |
| VEROF | common speedwell (*Veronica officinalis* L.) |

TABLE 4.2a

Field Efficacy Study Results - Grand Summary

| CODE | NARROWLEAVES % CONTROL AT 1, 3, 7, 14, DAT | BROADLEAVES % CONTROL AT 1, 3, 7, 14, DAT |
|---|---|---|
| 737F2S | 48, 66, 80, 98 | 55, 68, 80, 97 |
| 022K8T | 73, 85, 90, 99 | 72, 78, 90, 99 |
| 451A2K | 81, 90, 97, 100 | 82, 95, 97, 100 |
| 452B9X | 73, 85, 96, 99 | 83, 91, 96, 100 |
| 453C7P | 86, 94, 97, 99 | 85, 95, 97, 100 |
| 454D4K | 82, 90, 94, 99 | 81, 92, 94, 100 |
| 455E8S | 79, 91, 92, 99 | 76, 86, 92, 99 |
| 456F6H | 69, 86, 89, 99 | 65, 77, 89, 99 |
| 457G1T | 37, 67, 84, 99 | 43, 66, 84, 97 |
| 998F3S | 61, 79, 82, 99 | 61, 70, 82, 99 |
| STD6 | 35, 82, 92, 97 | 44, 83, 92, 99 |
| STD7 | 1, 21, 67, 98 | 2, 22, 67, 100 |
| STD5 | 85, 99, 99, 96 | 93, 100, 99, 98 |

Discussion:

These data show that the formulations that contain 2% PA yield better early symptom development than formulations that contain 1 and 0.4% PA. Also that the formulations that contains NIS yield greater than early symptom development than no NIS, particularly when combined with PA and AMS. Lastly, the formulations that contain AMS yield better early symptom development than formulations with 1% AMS (or 2.6% Ammonium Nitrate) which have better development than no AMS.

TABLE 4.2b

Results of Field Efficacy Study of Standard and Experimental Glyphosate Formulations - Detailed Summary

| | SPECIES MEANS AT 1, ¾, 7, 14 DAT | | | | | | | |
|---|---|---|---|---|---|---|---|---|
| CODE | FESAR | POAPR | TRFPR | VEROF | CYNDA | DIGSO | EUPCP | POEPR |
| 737F2S | 18, 35, 69, 100 | 48, 83, 88, 100 | 88, 92, 96, 99 | 85, 92, 96, 100 | 65, 72, 88, 96 | 50, 87, 100, 100 | 47, 83, 100, 100 | 53, 90, 100, 100 |
| 998F3S | 30, 61, 82, 100 | 75, 95, 96, 100 | 86, 92, 98, 100 | 85, 96, 98, 100 | 65, 75, 85, 98 | 67, 90, 100, 100 | 73, 97, 100, 100 | 87, 100, 100, 100 |
| 022K8T | 52, 75, 93, 100 | 78, 96, 97, 100 | 88, 97, 97, 99 | 88, 97, 97, 100 | 68, 77, 88, 99 | 100, 100, 100, 100 | 100, 100, 100, 100 | 100, 100, 100, 100 |
| 451A2K | 60, 79, 93, 100 | 84, 97, 98, 100 | 91, 97, 99, 100 | 91, 99, 99, 100 | 88, 91, 97, 99 | 90, 90, 100, 100 | 73, 93, 100, 100 | 100, 100, 100, 100 |
| 452B9X | 43, 62, 93, 100 | 68, 94, 97, 100 | 88, 99, 99, 100 | 90, 99, 99, 100 | 85, 91, 96, 99 | 77, 87, 100, 100 | 90, 90, 100, 100 | 100, 100, 100, 100 |
| 453C7P | 68, 86, 97, 100 | 83, 98, 97, 100 | 91, 99, 96, 98 | 92, 99, 96, 100 | 92, 94, 96, 98 | 93, 100, 100, 100 | 100, 100, 100, 100 | 100, 100, 100, 100 |
| 454D4K | 60, 81, 95, 100 | 88, 98, 99, 100 | 92, 100, 100, 100 | 90, 100, 100, 100 | 83, 87, 94, 97 | 93, 100, 100, 100 | 100, 100, 100, 100 | 100, 100, 100, 100 |
| 455E8S | 66, 86, 95, 100 | 85, 99, 99, 100 | 91, 100, 98, 97 | 90, 100, 98, 100 | 76, 84, 91, 99 | 97, 100, 100, 100 | 100, 100, 100, 100 | 100, 100, 100, 100 |
| 456F6H | 61, 85, 95, 100 | 72, 96, 99, 100 | 87, 99, 98, 97 | 87, 98, 98, 100 | 70, 77, 87, 99 | 70, 87, 100, 100 | 83, 90, 100, 100 | 97, 100, 100, 100 |
| 457G1T | 29, 62, 87, 100 | 50, 81, 93, 100 | 68, 91, 98, 100 | 70, 90, 98, 100 | 46, 62, 80, 97 | 20, 77, 100, 100 | 17, 43, 90, 100 | 60, 100, 100, 100 |
| STD 6 | 29, 79, 91, 98 | 17, 86, 94, 98 | 33, 93, 95, 98 | 38, 93, 95, 100 | 48, 84, 94, 95 | 47, 100, 100, 100 | 0, 90, 100, 100 | 40, 100, 100, 100 |
| STD 7 | 2, 12, 55, 99 | 3, 40, 84, 100 | 2, 47, 94, 100 | 2, 47, 94, 100 | 2, 16, 67, 97 | 0, 23, 100, 100 | 0, 0, 80, 100 | 0, 17, 50, 100 |

TABLE 4.2b-continued

Results of Field Efficacy Study of Standard and Experimental Glyphosate Formulations - Detailed Summary

| | | | | | | | | |
|---|---|---|---|---|---|---|---|---|
| STD 5 | 74, 99, 99, 99 | 57, 98, 99, 97 | 73, 98, 96, 95 | 70, 98, 96, 100 | 97, 99, 99, 95 | 100, 100, 100, 100 | 100, 100, 100, 100 | 100, 100, 100, 100 |

SPECIES MEANS AT 1, ¾, 7, 14 DAT

| CODE | LIPNO | PASUR | FESAW | PASDI | ANDGL | ASCLA | DICCA | GRAND MEAN |
|---|---|---|---|---|---|---|---|---|
| 737F2S | 33, 20, 50, 100 | 67, 100, 100, 100 | 18, 47 | 81, 87, 89, 97 | 73, 80, 74, 100 | 65, 80, 0, 100 | 5, 12, 25, 73 | 51, 67, 83, 98 |
| 998F3S | 40, 20, 50, 100 | 80, 100, 100, 100 | 70, 91 | 89, 95, 96, 99 | 28, 45, 82, 100 | 80, 90, 0, 100 | 5, 7, 28, 88 | 61, 75, 86, 99 |
| 022K8T | 57, 50, 87, 100 | 87, 100, 100, 100 | 82, 93 | 97, 97, 97, 99 | 57, 83, 97, 99 | 0, 0, 0, 100 | 5, 12, 25, 93 | 72, 82, 92, 99 |
| 451A2K | 60, 83, 90, 100 | 87, 100, 100, 100 | 82, 92 | 94, 95, 94, 100 | 92, 95, 100, 100 | 96, 100, 0, 100 | 54, 92, 84, 100 | 81, 92, 97, 100 |
| 452B9X | 90, 100, 100, 100 | 90, 100, 100, 100 | 77, 92 | 92, 97, 95, 99 | 85, 83, 98, 99 | 93, 100, 0, 100 | 28, 55, 70, 99 | 77, 87, 96, 100 |
| 453C7P | 90, 100, 100, 100 | 100, 100, 100, 100 | 87 96 | 95, 98, 98, 99 | 92, 90, 99, 100 | 90, 98, 0, 100 | 31, 71, 87, 99 | 86, 94, 97, 99 |
| 454D4K | 87, 100, 100, 100 | 100, 100, 100, 100 | 88, 96 | 99, 97, 98,99 | 72, 90, 100, 100 | 90, 0, 0, 100 | 20, 52, 40, 97 | 81, 91, 95, 99 |
| 455E8S | 87, 100, 100, 100 | 90, 100, 100, 100 | 83, 95 | 95, 97, 98, 99 | 42, 70, 80, 100 | 87, 95, 0, 100 | 11, 18, 45, 95 | 78, 89, 94, 99 |
| 456F6H | 77, 100, 100, 100 | 90, 100, 100, 100 | 42, 90 | 89, 96, 97, 99 | 17, 43, 70, 100 | 0, 0, 0, 100 | 7, 12, 30, 93 | 67, 83, 92, 99 |
| 457G1T | 53, 83, 100, 100 | 30, 90, 100, 100 | 18, 43 | 62, 77, 92, 99 | 21, 28, 47, 97 | 48, 73, 0, 100 | 2, 8, 33, 80 | 39, 67, 86, 98 |
| STD 6 | 43, 27, 63, 100 | 43, 100, 100, 100 | 18, 83 | 13, 42, 87, 98 | 63, 73, 92, 98 | 58, 95, 0, 100 | 100, 95, 100, 100 | 38, 82, 93, 98 |
| STD 7 | 0, 10, 33, 100 | 0, 40, 100, 100 | 0, 20 | 3, 23, 80, 99 | 5, 28, 58, 100 | 5, 18, 0, 100 | 3, 11, 45, 100 | 2, 21, 71, 99 |
| STD 5 | 100, 100, 100, 100 | 100, 100, 100, 100 | 67, 97 | 88, 94, 92, 86 | 98, 100, 100, 99 | 100, 100, 0, 100 | 99, 100, 100, 90 | 88, 99, 99, 97 |

TABLE 4.2c

Results of Field Efficacy Study of Standard and Experimental Glyphosate Formulations

| CODE | TRFRE | FESAR | POAPW | PLALA | TTTTT |
|---|---|---|---|---|---|

SPECIES MEANS AT 1, 5 & 9 HAT (HOUR AFTER TREATMENT) AND 1, 2, 5, 8, 14, 29 DAT respectively

| CODE | TRFRE | FESAR | POAPW | PLALA | TTTTT |
|---|---|---|---|---|---|
| 295L1V | 3, 63, 62, 68, 76, 82, 91, 100, 100 | 0, 7, 27, 32, 45, 45, 99, 100, 100 | 0, 15, 33, 40, 53, 55, 99, 100, 100 | 10, 20, 40, 48, 52, 47, 98, 100, 100 | 5, 37, 48, 55, 55, 62, 96, 100, 100 |
| 451A2K | 3, 87, 89, 94, 95, 94, 91, 99, 100, 100 | 0, 18, 28, 58, 77, 77, 99, 100, 100 | 0, 38, 50, 79, 91, 90, 99, 100, 100 | 10, 81, 94, 98, 94, 90, 99, 100, 100 | 7, 72, 73, 84, 87, 88, 96, 99, 100, 100 |
| 453C7P | 8, 91, 95, 98, 98, 97, 92, 100, 100 | 3, 53, 88, 92, 94, 91, 100, 100, 100 | 3, 75, 90, 97, 97, 97, 100, 100, 100 | 22, 91, 97, 99, 95, 95, 100, 100, 100 | 10, 84, 91, 95, 95, 95, 97, 100, 100 |
| STD 8 | 0, 3, 7, 33, 35, 47, 98, 100, 100 | 0, 0, 7, 17, 23, 20, 99, 100, 100 | 0, 3, 7, 17, 28, 38, 99, 100, 70 | 0, 2, 10, 33, 28, 40, 99, 100, 100 | 0, 3, 7, 25, 28, 43, 98, 100, 100 |

TABLE 4.2d

Results of Field Efficacy Study of Standard and
Experimental Glyphosate Formulations - cont.

| CODE | TRFRE | DIORC | CYNDA | PLALA | TTTTT |
|---|---|---|---|---|---|
| | | SPECIES MEANS AT 1, 5 & 9 HAT | | | |
| | | (HOUR AFTER TREATMENT) | | | |
| | | AND 1, 3, 7, 14, 28 DAT | | | |
| 295L1V | 18, 30, 33, 40, 58, 68, 69, 73 | 15, 18, 23, 25, 30, 38, 67, 92 | 12, 17, 18, 17, 20, 25, 89, 90 | 8, 18, 15, 28, 20, 30, 100 | 18, 30, 33, 40, 47, 59, 70, 69 |
| 451A2K | 23, 35, 40, 47, 70, 75, 75, 78 | 18, 22, 30, 38, 42, 55, 76, 95 | 13, 20, 30, 35, 40, 43, 92, 84 | 28, 48, 53, 53, 58, 55, 100 | 23, 38, 42, 50, 58, 68, 79, 72 |
| 453C7P | 28, 45, 47, 55, 76, 69, 71, 72 | 20, 33, 45, 48, 52, 62, 87, 97 | 15, 40, 48, 52, 62, 65, 93, 71 | 30, 58, 64, 68, 79, 79, 100 | 32, 48, 52, 61, 68, 74, 73, 69 |
| STD 8 | 0, 2, 13, 17, 23, 48, 75, 88 | 0, 5, 8, 20, 22, 35, 68, 95 | 10, 2, 10, 20, 15, 25, 92, 87 | 0, 0, 8, 20, 18, 30, 94 | 0, 3, 15, 18, 23, 52, 78, 81 |

Discussion:

The field tests in Tables 4.2c-4.2d show data comparing formulations with No PA (STD8), PA alone (295L1V), PA+AMS (451A2K) and PA+AMS+NIS (453C7P). The data clearly shows the benefit of PA to fast symptom development over no PA. Also noted is the advantage to fast symptom development when AMS is added to the formulation. The advantage overall to the formulation containing all three components (PA+AMS+NIS) is evident.

TABLE 4.2e

Results of Field Efficacy Study of Standard and
Experimental Glyphosate Formulations - with or without Imazapic

| CODE | FESAR 1, 3, 7, 15, 31 DAT | POAPW 1, 3, 7, 15, 31 DAT | TRFRE 1, 3, 7, 15, 31 DAT | TAROF 1, 3, 7, 15, 31 DAT | TTTTT 1, 3, 7, 15, 31 DAT |
|---|---|---|---|---|---|
| 295L1V | 52, 77, 85, 97, 100 | 75, 91, 90, 99, 100 | 88, 84, 80, 83, 92 | 78, 87, 80, 89, 100 | 80, 86, 82, 88, 96 |
| 451A2K | 90, 83, 90, 98, 100 | 95, 96, 95, 98, 100 | 88, 87, 82, 86, 88 | 89, 86, 81, 91, 100 | 92, 91, 86, 91, 93 |
| 489H1P | 91, 89, 93, 98, 100 | 95, 95, 97, 99, 100 | 95, 92, 88, 87, 88 | 92, 90, 90, 94, 100 | 95, 94, 94, 93, 94 |
| 490K9E | 87, 88, 89, 97, 100 | 95, 96, 95, 99, 100 | 89, 87, 77, 78, 79 | 88, 88, 79, 91, 100 | 92, 90, 86, 85, 87 |

| CODE | TTTTT % weed free at 31, 46, 60, and 90 DAT respectively |
|---|---|
| 295L1V | 93, 62, 5, 4 |
| 451A2K | 92, 67, 37, 0 |
| 489H1P | 94, 98, 97, 89 |
| 490K9E | 84, 91, 91, 62 |

Discussion:

This test demonstrates that adding imazapic as an active ingredient into this type of formulation does not interfere with the fast symptom development when the formulation contains either (PA+AMS) or (PA+AMS+NIS).

5. Study of the Effect of pH on Efficacy of Glysphosate Formulations

Experimental formulations were prepared at different pH values as in Table 5.1 and were evaluated under Greenhouse Study protocols as previously described. The results are summarized in Table 5.2. Data reported is % control at 1, 3, 6 Hours after treatment (HAT) and 1, 3, 7, 14, 24 DAT, respectively, for each species (treated vs. untreated control).

TABLE 5.1

Glyphosate Formulations Prepared to Demonstrate pH
Effect on Efficacy of the Formulation

| | Example | | | | | |
|---|---|---|---|---|---|---|
| | 1 | 2 | 3 | 4 | 5 | 6 |
| | pH 7.1 | pH 7.3 | pH 7.4 | pH 7.5 | pH 7.6 | pH 7.8 |
| Component | Weight of component (g) | | | | | |
| 62% solution Glyphosate of IPA | 32.2 | 32.2 | 32.2 | 32.2 | 32.2 | 32.2 |
| TOMADOL 1-7 | 15 | 15 | 15 | 15 | 15 | 15 |
| Antimicrobial (OTH2) | 1 | 1 | 1 | 1 | 1 | 1 |
| Pelargonic Acid | 20 | 20 | 20 | 20 | 20 | 20 |
| 45% KOH | 21.5 | 22.8 | 23.4 | 24 | 24.3 | 25.1 |
| Ammonium Sulfate | 20 | 20 | 20 | 20 | 20 | 20 |
| Antifoam (OTH3) | 0.1 | 0.1 | 0.1 | 0.1 | 0.1 | 0.1 |
| Water | 892 | 889 | 888.4 | 887.9 | 887.5 | 886.6 |
| Total | 1001.8 | 1000.1 | 1000.1 | 1000.2 | 1000.1 | 1000 |

TABLE 5.2

Results of Greenhouse Efficacy Study of
Experimental Glyphosate Formulations at varied pH

| Formulation | pH | DIGSA | POROL | FESAR | TRFRE |
|---|---|---|---|---|---|
| | | at 1, 3, 6 Hours (HAT) and 1, 3, 7, 14, 24 days (DAT) respectively for each species | | | |
| 1 | 7.1 | 35, 50, 65, 89, 97, 97, 95, 97 | 32, 48, 60, 78, 73, 77, 83, 84 | 15, 40, 57, 70, 82, 82, 83, 92 | 62, 73, 77, 79, 82, 73, 73, 70 |
| 2 | 7.3 | 40, 45, 57, 87, 93, 94, 98, 99 | 38, 50, 67, 72, 73, 85, 95, 100 | 13, 38, 53, 65, 79, 85, 92, 99 | 62, 73, 73, 76, 83, 72, 68, 62 |
| 3 | 7.4 | 35, 40, 50, 85, 86, 90, 98, 98 | 37, 50, 60, 70, 77, 80, 92, 98 | 12, 30, 48, 63, 73, 78, 84, 97 | 62, 73, 77, 76, 78, 69, 67, 55 |
| 4 | 7.5 | 37, 43, 52, 78, 80, 83, 93, 100 | 32, 45, 52, 72, 70, 80, 91, 97 | 15, 72, 42, 60, 73, 81, 85, 97 | 63, 72, 74, 77, 81, 73, 68, 73 |
| 5 | 7.6 | 38, 43, 50, 85, 88, 90, 95, 97 | 35, 45, 58, 75, 70, 80, 87, 96 | 13, 35, 50, 71, 78, 87, 91, 99 | 63, 70, 75, 75, 79, 68, 65, 60 |
| 6 | 7.8 | 38, 45, 53, 89, 91, 90, 98, 98 | 37, 50, 60, 72, 75, 84, 94, 99 | 18, 35, 53, 72, 78, 88, 93, 95 | 63, 70, 75, 77, 81, 72, 63, 60 |

Discussion:

The greenhouse data in Table 5.2 show data comparing formulations containing 2% IPA glyphosate, 2% PA, 2% AMS, 1.5% NIS with pH varied from 7.1 to 7.8. The data clearly shows that there is no effect in the fast symptom development or long term control on any of the test species as the pH changes.

6. Study of the Effect of Ammonium Sulfate on Efficacy of Glyphosate Formulations with Varying pH Experimental formulations were prepared at different pH values with or without ammonium sulfate as in Table 6.1 and were evaluated under Greenhouse Study protocols as previously described. The results are summarized in Table 6.2. Data reported is % control at 1, 3, 7, 14, 21 DAT, respectively, for each species (treated vs. untreated control).

TABLE 6.1

Glyphosate Formulations Prepared to Demonstrate pH Effect, with or without Ammonium Sulfate, on Efficacy of the Formulation Formulations with ammonium sulfate

| | Example | | | |
|---|---|---|---|---|
| | 1a | 2a | 3a | 4a |
| | pH 7.0 | pH 7.2 | pH 7.4 | pH 7.6 |
| Component | Weight of component (g) | | | |
| 62% IPA Glyphsoate solution | 32.2 | 32.2 | 32.2 | 32.2 |
| Surfactant (SUB2) | 5 | 5 | 5 | 5 |
| Antimicrobial (OTH2) | 1 | 1 | 1 | 1 |
| Pelargonic Acid | 20 | 20 | 20 | 20 |
| 45% KOH | 24.2 | 25.1 | 28.1 | 29.6 |
| Ammonium Sulfate | 20 | 20 | 20 | 20 |
| Antifoam (OTH3) | 0.1 | 0.1 | 0.1 | 0.1 |
| Water | 897.5 | 896.6 | 893.8 | 891.4 |
| Total | 1000.0 | 1000.0 | 1000.2 | 999.3 |

Formulations without ammonium sulfate

| | Example | | | |
|---|---|---|---|---|
| | 1b | 2b | 3b | 4b |
| | pH 7.0 | pH 7.2 | pH 7.4 | pH 7.6 |
| Component | Weight of component (g) | | | |
| 62% IPA Glyphsoate solution | 32.3 | 32.3 | 32.3 | 32.3 |
| Surfactant (SUB2) | 5 | 5 | 5 | 5 |
| Antimicrobial (OTH2) | 0.3 | 0.3 | 0.3 | 0.3 |
| Pelargonic Acid | 20 | 20 | 20 | 20 |
| 45% KOH | 25.0 | 26.3 | 28.5 | 29.6 |
| Propylene Glycol | 6.6 | 6.6 | 6.6 | 6.6 |
| Water | 912.9 | 909.6 | 907.2 | 906.3 |
| Total | 1002.9 | 1000.1 | 999.9 | 1000.1 |

TABLE 6.2

Results of Greenhouse Efficacy Study of Experimental Glyphosate Formulations at varied pH

| Formulation | pH | DIGSA | POROL | FESAR | TRFRE |
|---|---|---|---|---|---|
| | | at 1, 3, 7, 14, 21 DAT respectively | | | |
| 1a | 7.0 | 76, 77, 81, 79, 93 | 75, 85, 83, 89, 100 | 65, 74, 77, 78, 90 | 65, 75, 75, 72, 85 |
| 2a | 7.2 | 76, 75, 84, 95, 100 | 73, 84, 90, 98, 100 | 67, 85, 93, 100, 100 | 68, 73, 85, 97, 100 |
| 3a | 7.4 | 80, 82, 88, 96, 100 | 72, 81, 88, 99, 100 | 69, 88, 93, 100, 100 | 63, 69, 83, 97, 98 |
| 4a | 7.6 | 79, 80, 88, 94, 99 | 77, 85, 93, 99, 100 | 74, 93, 97, 100, 100 | 65, 66, 78, 88, 98 |
| 1b | 7.0 | 73, 74, 87, 97, 100 | 63, 70, 85, 98, 100 | 65, 75, 86, 97, 100 | 65, 66, 73, 81, 94 |
| 2b | 7.2 | 73, 70, 81, 92, 99 | 52, 55, 76, 93, 100 | 69, 81, 90, 100, 100 | 60, 65, 75, 87, 94 |
| 3b | 7.4 | 62, 63, 72, 78, 93 | 50, 52, 76, 98, 100 | 60, 68, 86, 98, 100 | 62, 64, 72, 82, 95 |
| 4b | 7.6 | 62, 67, 75, 77, 90 | 42, 47, 62, 76, 98 | 53, 63, 78, 85, 97 | 65, 71, 77, 81, 98 |

Discussion:

Table 6.2 shows the data from a greenhouse test of the formulations listed in Table 6.1. The data clearly demonstrates that formulations 1b-4b show slower development of symptoms as the pH rises from 7.0 to 7.6. The formulations 1a-4a show little to no effect in fast symptom development as the pH rises. The data also demonstrates that formulations 1a-4a generally give much better control particularly at 1 and 3 DAT than formulations 1b-4b.

The present invention is not limited to the above embodiments and can be variously modified. The above description of the preferred embodiments, including the Examples, is intended only to acquaint others skilled in the art with the invention, its principles, and its practical application so that others skilled in the art may adapt and apply the invention in its numerous forms, as may be best suited to the requirements of a particular use.

With reference to the use of the word(s) comprise or comprises or comprising in this entire specification (including the claims below), unless the context requires otherwise, those words are used on the basis and clear understanding that they are to be interpreted inclusively, rather than exclusively, and that each of those words is to be so interpreted in construing this entire specification.

What is claimed is:

1. An aqueous ready-to-use herbicidal composition useful for killing or controlling the growth of unwanted plants, comprising:
   from about 0.1% to about 5% by weight (a.e.) of a glyphosate component comprising N-(phosphonomethyl)glycine, an agronomically acceptable salt of N-(phosphonomethyl)glycine or a mixture thereof;
   from about 1.5% to about 5% by weight (a.e.) of a fatty acid component comprising more than 50% by weight of at least one $C_8$ to $C_{12}$ saturated, straight or branched chain fatty acid or an agronomically acceptable salt thereof; and
   from about 0.5% to about 4% by weight of an agronomically acceptable inorganic ammonium salt.

2. The ready-to-use herbicidal composition according to claim 1 wherein the agronomically acceptable inorganic ammonium salt is selected from the group consisting of ammonium sulfate, ammonium nitrate, ammonium thiocyanate, ammonium phosphate, ammonium chloride and mixtures thereof.

3. The ready-to-use herbicidal composition according to claim 2 wherein the agronomically acceptable inorganic ammonium salt is ammonium sulfate.

4. The ready-to-use herbicidal composition according to claim 3 comprising from about 1.5% to about 3% by weight of ammonium sulfate.

5. The ready-to-use herbicidal composition according to claim 1 wherein the fatty acid component comprises more than 50% by weight pelargonic acid or an agronomically acceptable salt thereof.

6. The ready-to-use herbicidal composition according to claim 5 wherein the fatty acid component comprises at least about 90% by weight pelargonic acid or an agronomically acceptable salt thereof.

7. The ready-to-use herbicidal composition according to claim 1 comprising from about 1.5% to about 3% by weight (a.e.) of the fatty acid component.

8. The ready-to-use herbicidal composition according to claim 3 comprising from about 2% to about 5% by weight (a.e.) of the fatty acid component and from about 2% to about 4% by weight of ammonium sulfate.

9. The ready-to-use herbicidal composition according to claim 1 wherein the glyphosate component comprises more than 50% by weight of an agronomically acceptable salt of N-(phosphonomethyl)glycine.

10. The ready-to-use herbicidal composition according to claim 9 wherein the glyphosate component comprises more than 50% by weight of a salt of N-(phosphonomethyl)glycine selected from the potassium, monoammonium, diammonium, sodium, monoethanolammonium, n-propylammonium, isopropylammonium, ethylammonium, dimethylammonium, ethylenediamine, hexamethylenediamine and trimethylsulfonium salts of N-(phosphonomethyl)glycine and combinations thereof.

11. The ready-to-use herbicidal composition according to claim 10 wherein the glyphosate component comprises more than 50% by weight of a salt of N-(phosphonomethyl)glycine selected from the isopropylammonium salt of N-(phosphonomethyl)glycine, the ammonium salt of N-(phosphonomethyl)glycine and the potassium salt of N-(phosphonomethyl)glycine.

12. The ready-to-use herbicidal composition according to claim 1 wherein the concentration of the glyphosate component is from about 1% to about 5% by weight (a.e.).

13. The ready-to-use herbicidal composition according to claim 12 wherein the concentration of the glyphosate component is from about 1% to about 2% by weight (a.e.).

14. The ready-to-use herbicidal composition according to claim 1 wherein the composition has a pH of from about 7.1 to about 7.6.

15. The ready-to-use herbicidal composition according to claim 1 further comprising a water-soluble surfactant component.

16. The ready-to-use herbicidal composition according to claim 1 further comprising one or more ingredients selected from the group consisting of additional herbicidal active ingredients, foam-moderating agents, preservatives, antifreeze agents, solubility-enhancing agents, dyes, pH adjusters and thickening agents.

17. The ready-to-use herbicidal composition according to claim 16 wherein the additional herbicidal active ingredient is selected from water-soluble forms of (2,4-dichlorophenoxy) acetic acid (2,4-D), 4-(2,4-dichlorophenoxy)butanoic acid (2,4-DB), (4-chloro-2-methylphoenoxy)acetic acid (MCPA), dicamba, diquat bromide, glufosinate, imazapic, imazapyr, imazethapyr, triclopyr and mixtures thereof.

18. An aqueous ready-to-use herbicidal composition useful for killing or controlling the growth of unwanted plants, comprising:

from about 0.1% to about 5% by weight (a.e.) of a glyphosate component comprising N-(phosphonomethyl)glycine, an agronomically acceptable salt of N-(phosphonomethyl)glycine or a mixture thereof;

from about 0.25% to about 5% by weight (a.e.) of a fatty acid component comprising more than 50% by weight of at least one $C_8$ to $C_{12}$ saturated, straight or branched chain fatty acid or an agronomically acceptable salt thereof; and from about 1% to about 4% by weight of ammonium sulfate.

19. The ready-to-use herbicidal composition according to claim 18 comprising from about 1.5% to about 3% by weight of ammonium sulfate.

20. The ready-to-use herbicidal composition according to claim 18 wherein the fatty acid component comprises more than 50% by weight pelargonic acid or an agronomically acceptable salt thereof.

21. The ready-to-use herbicidal composition according to claim 20 wherein the fatty acid component comprises at least about 90% by weight pelargonic acid or an agronomically acceptable salt thereof.

22. The ready-to-use herbicidal composition according to claim 18 comprising from about 1.5% to about 3% by weight (a.e.) of the fatty acid component.

23. The ready-to-use herbicidal composition according to claim 18 comprising from about 2% to about 4% by weight (a.e.) of the fatty acid component and from about 2% to about 4% by weight of ammonium sulfate.

24. The ready-to-use herbicidal composition according to claim 18 wherein the glyphosate component comprises more than 50% by weight of an agronomically acceptable salt of N-(phosphonomethyl)glycine.

25. The ready-to-use herbicidal composition according to claim 24 wherein the glyphosate component comprises more than 50% by weight of a salt of N-(phosphonomethyl)glycine selected from the potassium, monoammonium, diammonium, sodium, monoethanolammonium, n-propylammonium, isopropylammonium, ethylammonium, dimethylammonium, ethylenediamine, hexamethylenediamine and trimethylsulfonium salts of N-(phosphonomethyl)glycine and combinations thereof.

26. The ready-to-use herbicidal composition according to claim 25 wherein the glyphosate component comprises more than 50% by weight of a salt of N-(phosphonomethyl)glycine selected from the isopropylammonium salt of N-(phosphonomethyl)glycine, the ammonium salt of N-(phosphonomethyl)glycine and the potassium salt of N-(phosphonomethyl)glycine.

27. The ready-to-use herbicidal composition according to claim 18 wherein the concentration of the glyphosate component is from about 1% to about 5% by weight (a.e.).

28. The ready-to-use herbicidal composition according to claim 27 wherein the concentration of the glyphosate component is from about 1% to about 2% by weight (a.e.).

29. The ready-to-use herbicidal composition according to claim 18 wherein the composition has a pH of from about 7.1 to about 7.6.

30. The ready-to-use herbicidal composition according to claim 18 further comprising a water-soluble surfactant component.

31. The ready-to-use herbicidal composition according to claim 18 further comprising one or more ingredients selected from the group consisting of additional herbicidal active ingredients, foam-moderating agents, preservatives, antifreeze agents, solubility-enhancing agents, dyes, pH adjusters and thickening agents.

32. The ready-to-use herbicidal composition according to claim 31 wherein the additional herbicidal active ingredient is selected from water-soluble forms of (2,4-dichlorophenoxy) acetic acid (2,4-D), 4-(2,4-dichlorophenoxy)butanoic acid (2,4-DB), (4-chloro-2-methylphoenoxy)acetic acid (MCPA), dicamba, diquat bromide, glufosinate, imazapic, imazapyr, imazethapyr, triclopyr and mixtures thereof.

33. The composition of claim 1 further comprising a nonionic surfactant component comprising an alkoxylated, $C_8$ to $C_{20}$, nonaromatic alcohol with an average degree of alkoxylation such that the alcohol has a solubility in water of at least about 0.5% by weight at 25° C.

34. The herbicidal composition according to claim 33 wherein the alkoxylated, $C_8$ to $C_{20}$, nonaromatic alcohol has an average degree of alkoxylation of from about 2 to about 20.

35. The herbicidal composition according to claim 34 wherein the nonionic surfactant component comprises an ethoxylated, $C_8$ to $C_{20}$, nonaromatic alcohol with an average degree of ethoxylation from about 3 to about 12.

36. The herbicidal composition according to claim 35 wherein the nonionic surfactant component comprises an ethoxylated, primary or secondary, linear or minimally branched $C_{10}$ to $C_{14}$ alcohol having no more than 2 methyl substituents and an average degree of ethoxylation of from about 5 to about 9.

37. The herbicidal composition according to claim 36 wherein the nonionic surfactant component comprises more than 50% by weight ethoxylated, primary or secondary, undecyl alcohol with an average degree of ethoxylation of from about 5 to about 9.

38. The herbicidal composition according to claim 37 wherein the undecyl alcohol that predominates the nonionic surfactant component is ethoxylated, primary, linear undecyl alcohol.

39. The herbicidal composition according to claim 38 wherein the nonionic surfactant component comprises at least about 90% by weight ethoxylated, primary, linear undecyl alcohol having an average degree of ethoxylation of about 7.

40. The composition of claim 18 further comprising a nonionic surfactant component comprising an alkoxylated, $C_8$ to $C_{20}$, nonaromatic alcohol with an average degree of alkoxylation such that the alcohol has a solubility in water of at least about 0.5% by weight at 25° C.

41. The herbicidal composition according to claim 40 wherein the alkoxylated, $C_8$ to $C_{20}$, nonaromatic alcohol has an average degree of alkoxylation of from about 2 to about 20.

42. The herbicidal composition according to claim 41 wherein the nonionic surfactant component comprises an ethoxylated, $C_8$ to $C_{20}$, nonaromatic alcohol with an average degree of ethoxylation from about 3 to about 12.

43. The herbicidal composition according to claim 42 wherein the nonionic surfactant component comprises an ethoxylated, primary or secondary, linear or minimally branched $C_{10}$ to $C_{14}$ alcohol having no more than 2 methyl substituents and an average degree of ethoxylation of from about 5 to about 9.

44. The herbicidal composition according to claim 43 wherein the nonionic surfactant component comprises more than 50% by weight ethoxylated, primary or secondary, undecyl alcohol with an average degree of ethoxylation of from about 5 to about 9.

45. The herbicidal composition according to claim 44 wherein the undecyl alcohol that predominates the nonionic surfactant component is ethoxylated, primary, linear undecyl alcohol.

46. The herbicidal composition according to claim 45 wherein the nonionic surfactant component comprises at least about 90% by weight ethoxylated, primary, linear undecyl alcohol having an average degree of ethoxylation of about 7.

* * * * *

UNITED STATES PATENT AND TRADEMARK OFFICE
CERTIFICATE OF CORRECTION

PATENT NO.         : 8,268,749 B2                                    Page 1 of 1
APPLICATION NO.    : 11/227577
DATED              : September 18, 2012
INVENTOR(S)        : Wright et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 394 days.

Signed and Sealed this
Third Day of November, 2015

Michelle K. Lee
*Director of the United States Patent and Trademark Office*